(12) United States Patent
Park et al.

(10) Patent No.: US 8,772,463 B2
(45) Date of Patent: Jul. 8, 2014

(54) FLUORESCENT DYE-LABELED GLUCOSE BIOPROBE, SYNTHESIS METHOD AND USAGE THEREOF

(75) Inventors: Seung Bum Park, Seoul (KR); Hyang Yeon Lee, Seoul (KR); Jong Min Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 131 days.

(21) Appl. No.: 12/876,520

(22) Filed: Sep. 7, 2010

(65) Prior Publication Data

US 2011/0059477 A1 Mar. 10, 2011

Related U.S. Application Data

(63) Continuation-in-part of application No. 12/532,913, filed as application No. PCT/KR2007/006713 on Dec. 21, 2007.

(30) Foreign Application Priority Data

| Mar. 26, 2007 | (KR) | 10-2007-0029334 |
| Sep. 7, 2009 | (KR) | 10-2009-0084068 |
| Mar. 18, 2010 | (KR) | 10-2010-0024274 |

(51) Int. Cl.
*C07H 17/02* (2006.01)

(52) U.S. Cl.
USPC ........................................... 536/17.4

(58) Field of Classification Search
None
See application file for complete search history.

(56) References Cited

U.S. PATENT DOCUMENTS

2010/0105149 A1 4/2010 Park et al.

OTHER PUBLICATIONS

Park, J. et al., Angew. Chem. Int. Ed., "Development of a Cy3-Labeled Glucose Bioprobe and Its Application in Bioimaging and Screening for Anticancer Agents", published online Feb. 7, 2007, vol. 46, pp. 2018-2022.*
Tian, Y. S. et al., Angewandte Chemie, "A Two-Photon Tracer for Glucose Uptake", published online Sep. 19, 2009, vol. 48, pp. 8027-8031.*
Zumbuehl, A. et al., Angewandte Chemie, "An Amphotericin B-Fluorescein Conjugate as a Powerful Probe for Biochemical Studies of the Membrane", 2004, vol. 116, pp. 5293-5297.*
Campbell, R.E. and Tanner, M.E., "UDP-Glucose Analogues as Inhibitors and Mechanistic Probes of UDP-Glucose Dehydrogenase," J. Org. Chem. (1999), 64, p. 9487-9492.
Cheng, Z. et al., "Near-Infrared Fluorescent Deoxyglucose Analogue for Tumor Optical Imaging in Cell Culture and Living Mice," Bioconjugate Chem. (2006), 17, p. 662-669.
Conti, P.S. et al., "PET and [$^{18}$F]-FDG in Oncology: A Clinical Update," Nuclear Medicine & Biology, (1996) vol. 23, p. 717-735.

Czernin, J. and Phelps, M.E., "Positron Emission Tomography Scanning: Current and Future Applications," Annu. Rev. Med. (2002), 53, p. 89-112.
Fazio, F. et al., "Synthesis of Sugar Arrays in Microtiter Plate," J. Am. Chem. Soc. (2002), 124, p. 14397-14402.
Hruz, P.W. and Mueckler, M.M., "Structural Analysis of the GLUT1 Facilitative Glucose Transporter (review)," Molecular Membrane Biology (2001), 18, p. 183-193.
Li, Y. et al., "Synthesis and Antimalarial Activity of Artemisinin Derivatives Containing an Amino Group," J. Med. Chem. (2000), 43, p. 1635-1640.
Maier, M.A. et al., "Synthesis of Antisense Oligonucleotides Conjugated to a Multivalent Carbohydrate Cluster for Cellular Targeting," Bioconjugate Chem. (2003), 14, p. 18-29.
Mosmann, T., "Rapid Colorimetric Assay for Cellular Growth and Survival: Application to Proliferation and Cytotoxicity Assays," Journal of Immunological Methods (1983), 65, p. 55-63.
Natarajan, A. and Srienc, F., "Glucose Uptake Rates of single *E. coli* cells grown in glucose-limited chemostat cultures," Journal of Microbiological Methods (2000), 42, p. 87-96.
O'Neil, R.G. et al., "Uptake of a Fluorescent Deoxyglucose Analog (2-NBDG) in Tumor Cells," Mol. Imaging Biol. (2005), 7, p. 388-392.
Portier, G. L. et al., "Differentiation Markers of Mouse $C_2C_{12}$ and Rat $L_6$ Myogenic Cell Lines and the Effect of the Differentiation Medium," In Vitro Cell Dev. Biol.-Animal (1999), 35, p. 219-227.
Som, P. et al., "A Fluorinated Glucose Analog, 2-fluoro-2-deoxy-D-glucose (F-18): Nontoxic Tracer for Rapid Tumor Detection," J. Nucl. Med (1980), 21, p. 670-675.
Trester-Zedlitz, M. et al., "A Modular Cross-Linking Approach for Exploring Protein Interactions," J. Am. Chem. Soc. (2003), 125, p. 2416-2425.
Wilson, C.M. et al., "Regulation of cell surface CLUT1, GLUT3, and GLUT4 by insulin and IGF-1 in L6 myotubes," FEBS Letters (1995) 368, p. 19-22.
Yamada, K. et al., "Measurement of Glucose Uptake and Intracellular Calcium Concentration in Single, Living Pancreatic β-Cells," Journal of Biological Chemistry (2000), 275(29), p. 22278-22283.
Ye, Y. et al., "Polyvalent Carbocyanine Molecular Beacons for Molecular Recognitions," J. Am. Chem. Soc. (2004), 126, p. 7740-7741.
Yorimitsu, H. et al., "Ultra-rapid Synthesis of $^{15}$O-Labeled 2-Deoxy-D-glucose for Positron Emission Tomography (PET)," Angew. Chem. Int. Ed. (2005), 44, p. 2708-2711.
Yoshioka, K. et al., "Intracellular Fate of 2-NBDG, a Fluorescent Probe for Glucose Uptake Activity, in *Escherichia coli* Cells," Biosci. Biotech. Biochem (1996), 60(11), p. 1899-1901.

(Continued)

*Primary Examiner* — Layla Bland
*Assistant Examiner* — Bahar Craigo
(74) *Attorney, Agent, or Firm* — Hamre, Schumann, Mueller & Larson, P.C.

(57) ABSTRACT

Disclosed are a novel fluorescent glucose analogue, a method for the synthesis thereof and the use thereof. The novel fluorescent glucose analogue is labeled with fluorescent dye by O-1-glycosylation and via various linkers. The fluorescent glucose analogue can be applied to molecular bioimaging and a method for screening curative or preventive drugs for glucose metabolism-related diseases.

3 Claims, 27 Drawing Sheets
(10 of 27 Drawing Sheet(s) Filed in Color)

(56) References Cited

OTHER PUBLICATIONS

Yoshioka, K. et al., "A Novel Fluorescent Derivative of Glucose Applicable to the Assessment of Glucose Uptake Activity of *Escherichia coli*," Biochimica et Biophysica Act (1996), 1289, p. 5-9.

Zhang, M. et al., "Pyropheophorbide 2-Deoxyglucosamide: A New Photosensitizer Targeting Glucose Transporters," Bioconjugate Chem. (2003), 14, p. 709-714.

Zhang, Z, et al., "Metabolic Imaging of Tumors Using Intrinsic and Extrinsic Fluorescent Markers," Biosensors and Bioelectronics (2004), 20, p. 643-650.

\* cited by examiner a)

5 µM Cy3-Glc-a

5 µM GB2-Cy3

5 µM NBDG

50 µM NBDG b)

c)

(a)

(b)

FLUORESCENT DYE-LABELED GLUCOSE BIOPROBE, SYNTHESIS METHOD AND USAGE THEREOF

This application is a continuation-in-part of U.S. application Ser. No. 12/532,913, filed Sep. 24, 2009, the entire disclosures of all of which are incorporated herein by reference.

This application claims priority from Korean Patent Application Nos. 10-2007-0029334 filed on Mar. 26, 2007, 10-2009-0084068 filed on Sep. 7, 2009, and 10-2010-0024274 filed on Mar. 18, 2010 in the Korean Intellectual Property Office, the disclosure of which is incorporated herein by reference in its entirety.

BACKGROUND OF THE INVENTION

1. Field of the Invention

The present invention relates to a fluorescent dye-labeled glucose analogue, and a synthesis method and usage of the same, and more particularly, to a novel fluorescent glucose analogue labeled with fluorescent dye by O-1-glycosylation and via various linkers, a method for the synthesis thereof, and application thereof to molecular bioimaging and screening curative or preventive drugs for glucose metabolism-related diseases.

2. Description of the Related Art

Glucose is the most important energy source for cell growth; therefore, a fast-growing cancer cell requires more glucose than a normal cell. One of the biochemical markers of tumor malignancy is enhanced glycolysis due to the overexpression of glucose transporters (GLUTs) and the increased activity of hexokinases (phosphorylation catalytic enzyme of hexose) in tumors [M. Zhang, Z. Zhang, D. Blessington, H. Li, T. M. Busch, V. Madrak, J. Miles, B. Chance, J. D. Glickson, G. Zheng, *Bioconjugate Chem.* 2003, 14, 709-714].

The in vitro and in vivo assessment of glucose utilization has been of considerable interest to scientific communities, especially those in the biological and biomedical fields. One of the successful applications of this assessment is tumor diagnosis by positron emission tomography (PET) using a glucose probe of $^{18}$F 2-fluoro-2-deoxyglucose ($^{18}$FDG) where $^{18}$F (fluoride) is used as an isotope that emits a positron [P. Som, H. L. Atkins, D. Bandoypadhyay, J. S. Fowler, R. R. MacGregor, K. Matsui, Z. H. Oster, D. F. Sacker, C. Y. Shiue, H. Turner, C. N. Wan, A. P. Wolf, S. V. Zabinski, *J. Nucl. Med.* 1980, 21, 670-675; H. Yorimitsu, Y. Murakami, H. Takamatsu, S. Nishimura, E. Nakamura, *Angew. Chem. Int. Ed.* 2005, 44, 2708-2711]. PET with $^{18}$FDG is a molecular imaging modality that monitors metabolic perturbation in tumor cells and allows the imaging of the exact positions of tumors in the human body; therefore, it is widely applied in the diagnosis of various tumors [P. S. Conti, D. L. Lilien, K. Hawley, J. Keppler, S. T. Grafton, J. R. Bading, *Nucl, Med, Biol.* 1996, 23, 717-735; J. Czernin, M. E. Phelps, *Annu. Rev. Med.* 2002, 53, 89-112.].

A fluorescent 2-deoxyglucose analogue, i.e., 2-[N-(7-nitrobenz-2-oxa-1,3-diazol-4-yl)amino]-2-deoxy-D-glucose (2-NBDG), was developed and extensively studied, primarily by Yoshioka et al. [K. Yoshioka, H. Takahashi, T. Homma, M. Saito, K. B. Oh, Y. Nemoto, H. Matsuoka, *Biochim. Biophys. Acta.* 1996, 1289, 5-9.]. 2-NBDG has been widely applied in various studies, especially for tumor imaging and examination of GLUT-related cell metabolism [K. Yoshioka, H. Takahashi, T. Homma, M. Saito, K. B. Oh, Y. Nemoto, H. Matsuoka, *Biochim. Biophys. Acta.* 1996, 1289, 5-9; K. Yoshioka, M. Saito, K. B. Oh, Y. Nemoto, H. Matsuoka, M. Natsume, H. Abe, *Biosci. Biotech. Biochem.* 1996, 60, 1899-1901; A. Natarajan, F. Srienc, *J. Microbiol. Methods.* 2000, 42, 87-96]. In addition, some 2-deoxyglucose analogues have been reported [Z. Cheng, J. Levi, Z. Xiong, O. Gheysens, S. Keren, X. Chem, S. S. Gambhir, *Bioconjugate Chem.* 2006, 17, 662-669; Z. Zhang, H. Li, Q. Liu, L. Zhou, M. Zhang, Q. Luo, J. Glickson, B. Chance, G. Zheng, *Biosensors and Bioelectonics.* 2004, 20, 643-650; Y. Ye, S. Bloch, S. Achilefu, *J. Am. Chem. Soc,* 2004, 126, 7740-7741].

However, these analogues are all N-2-glycosylated analogues, and are disadvantageous in that a difference according to the type of α and β anomers of glucose cannot be confirmed, and that while D-glucose is an important energy source the cellular uptake of the analogues occurs only in a D-glucose-free medium, thus, it cannot be applied to test a cell in practice. Therefore, known 2-NBDG or N-2-glycosylated analogues cannot be used for screening anti-cancer drugs or therapeutics for obesity- or glucose metabolism-related diseases (e.g. diabetes).

Accordingly, the present inventors designed and synthesized novel glucose analogues labeled with fluorescent dye by O-1-glycosylation and via various linkers, unlike the known N-2-glycosylated glucose analogues.

SUMMARY OF THE INVENTION

Accordingly, an object of the present invention is to provide a novel fluorescent glucose analogue for analysis of the intracellular glucose uptake.

Another object of the present invention is to provide a method for the synthesis of the glucose analogue.

Yet another object of the present invention is to provide the use of the glucose analogue as a bioprobe and a method therefor.

In accordance with an aspect thereof, the present invention provides a fluorescent glucose analogue labeled with fluorescent dye by O-1-glycosylation and via various linkers including aliphatic, aromatic and heterocyclic rings.

In accordance with another aspect thereof, the present invention provides a method for the asymmetric synthesis of the fluorescent glucose analogue.

In accordance with a further aspect thereof, the present invention provides a bioprobe comprising the fluorescent glucose analogue.

In accordance with still a further aspect thereof, the present invention provides a molecular bioimaging method using the fluorescent glucose analogue as a bioprobe.

In accordance with still another aspect thereof, the present invention provides a FACS (fluorescent activated cell sorting) method using the fluorescent glucose analogue as a bioprobe.

In accordance with still yet another aspect thereof, the present invention provides a method for screening curative or preventive drugs for glucose metabolism-related diseases, using the fluorescent glucose analogue as a bioprobe.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which:

FIG. 14A is a graph that illustrates Cy3-Glc-α uptake by A549 cells, and the fluorescence intensities are expressed as arbitrary unit (a.u.) determined by continuous measurement from ROIs (Regions of Interest) in five independent cells marked on B based on unbiased selection. FIG. 14B illustrates merged phase-contrast image and fluorescence images in A549 cells captured by live-cell imaging with a confocal laser scanning microscope (CLSM), in which (a) illustrates A549 cells immediately after the Cy3-Glc-α treatment, and (b) illustrates A549 cells after 60 min after the Cy3-Glc-α treatment (Scale bar=20 µm).

DESCRIPTION OF THE PREFERRED EMBODIMENTS

Figure 1:
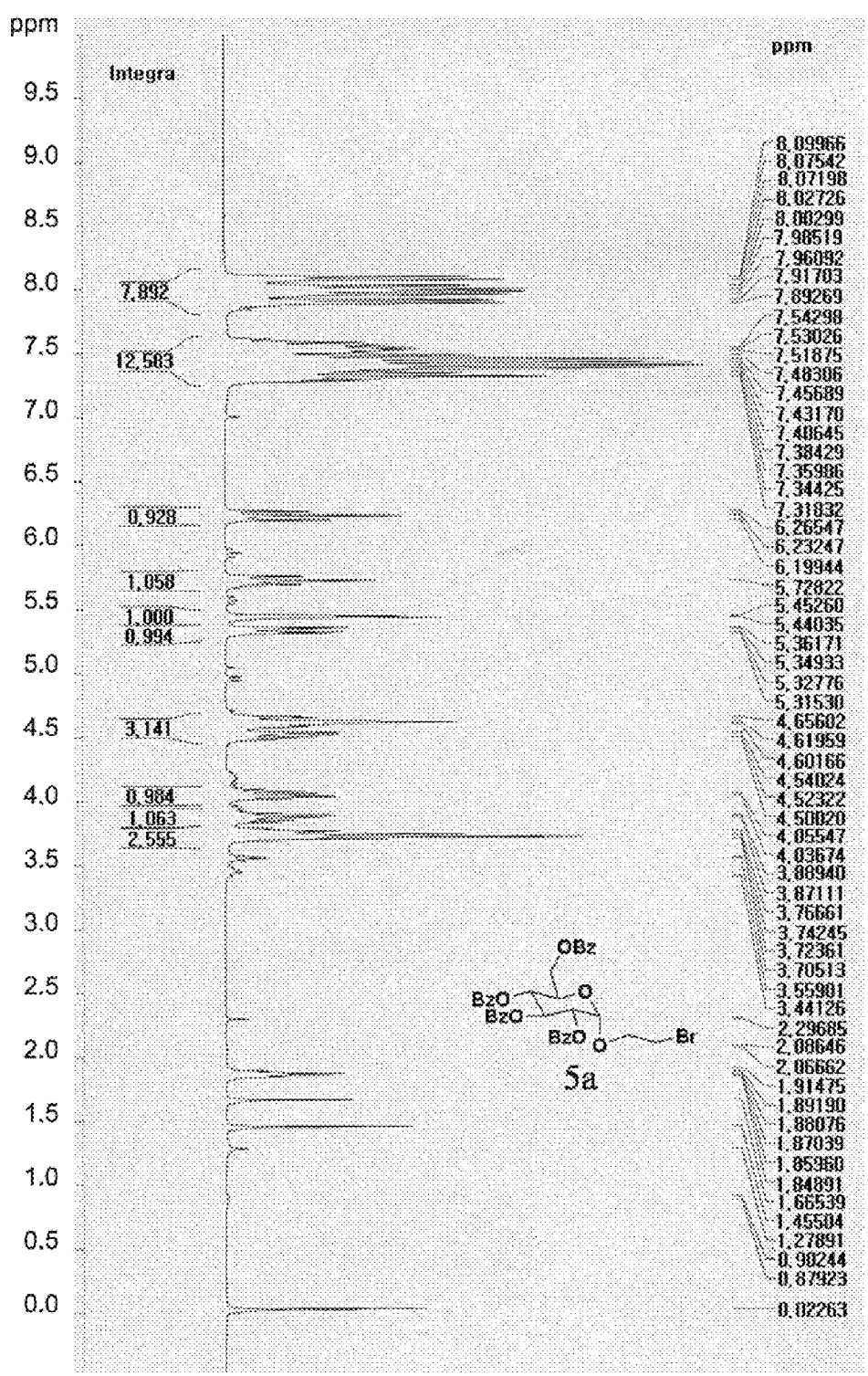
FIG. 1 illustrates $^1$H NMR data of a (2-bromoethyl)-2,3,4,6-tetra-O-benzoyl-α-D-glucoside (5a) compound that is an intermediate obtained in Example 1.
Figure 2:
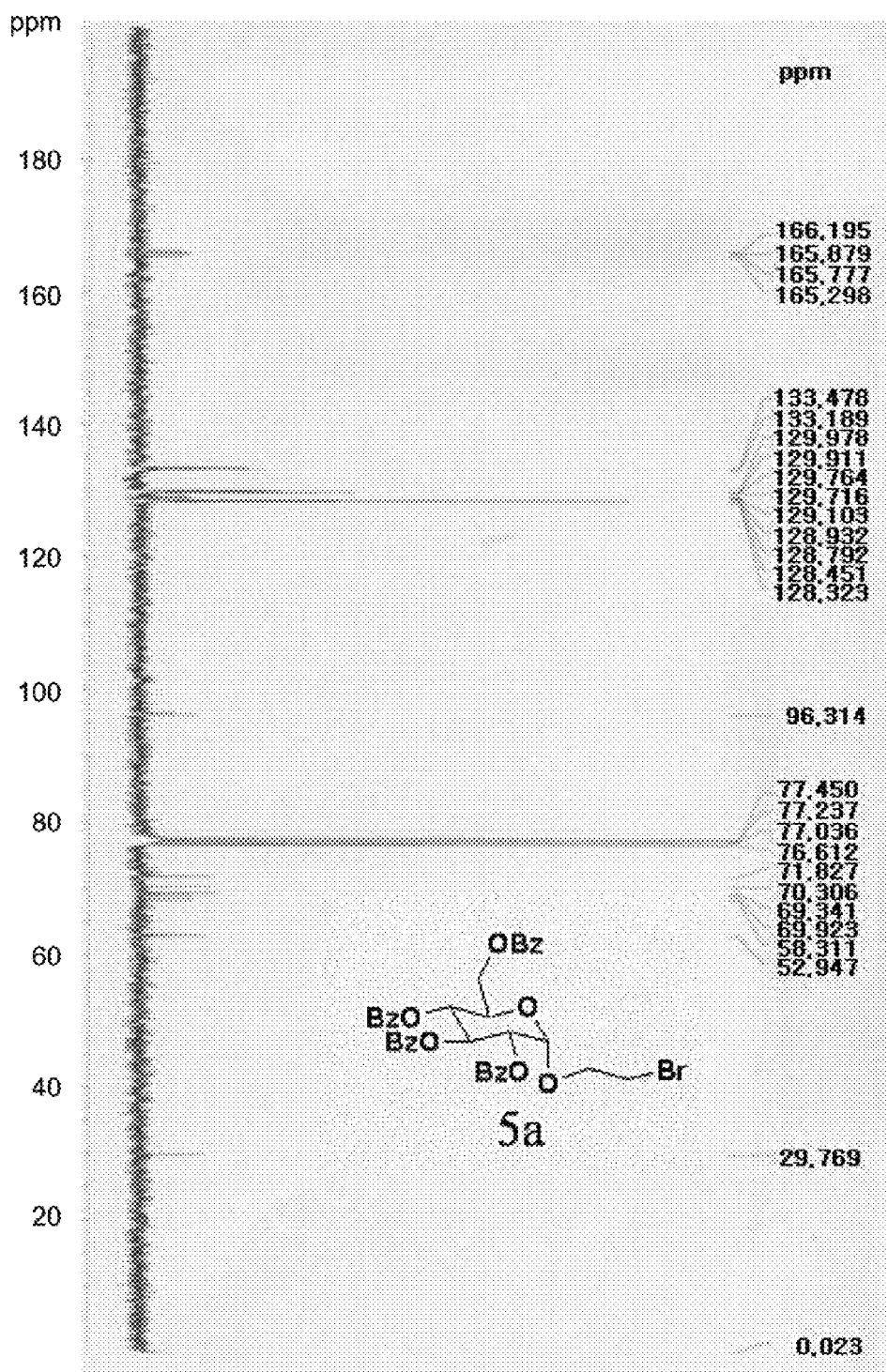
FIG. 2 illustrates $^{13}$C NMR data of a (2-bromoethyl)-2,3,4,6-tetra-O-benzoyl-α-D-glucoside (5a) compound that is an intermediate obtained in Example 1.
Figure 3:
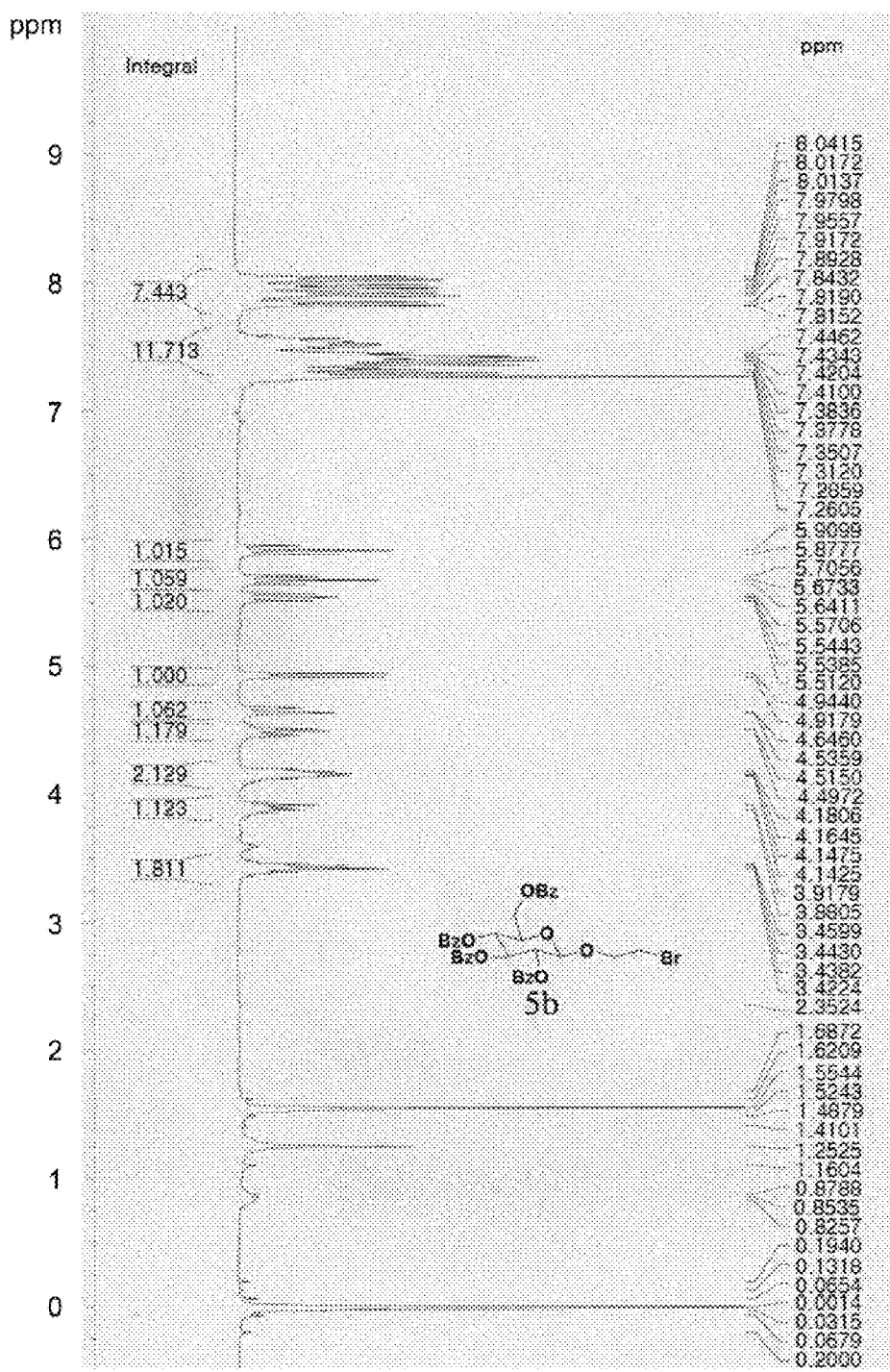
FIG. 3 illustrates $^1$H NMR data of a (2-bromoethyl)-2,3,4,6-tetra-O-benzoyl-β-D-glucoside (5b) compound that is an intermediate obtained in Example 1.
Figure 4:
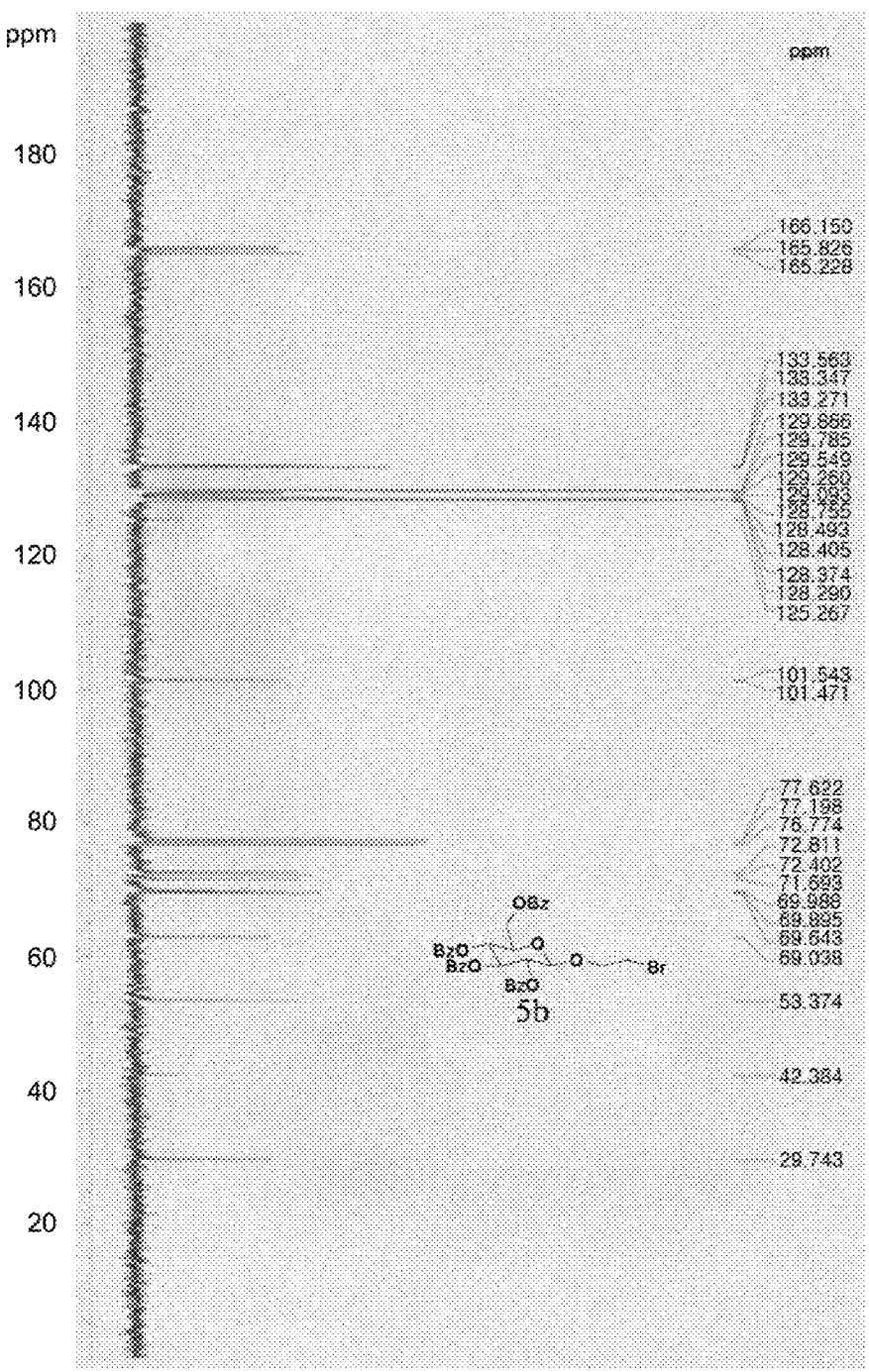
FIG. 4 illustrates $^{13}$NMR data of a (2-bromoethyl)-2,3,4,6-tetra-O-benzoyl-β-D-glucoside (5b) compound that is an intermediate obtained in Example 1.
Figure 5:
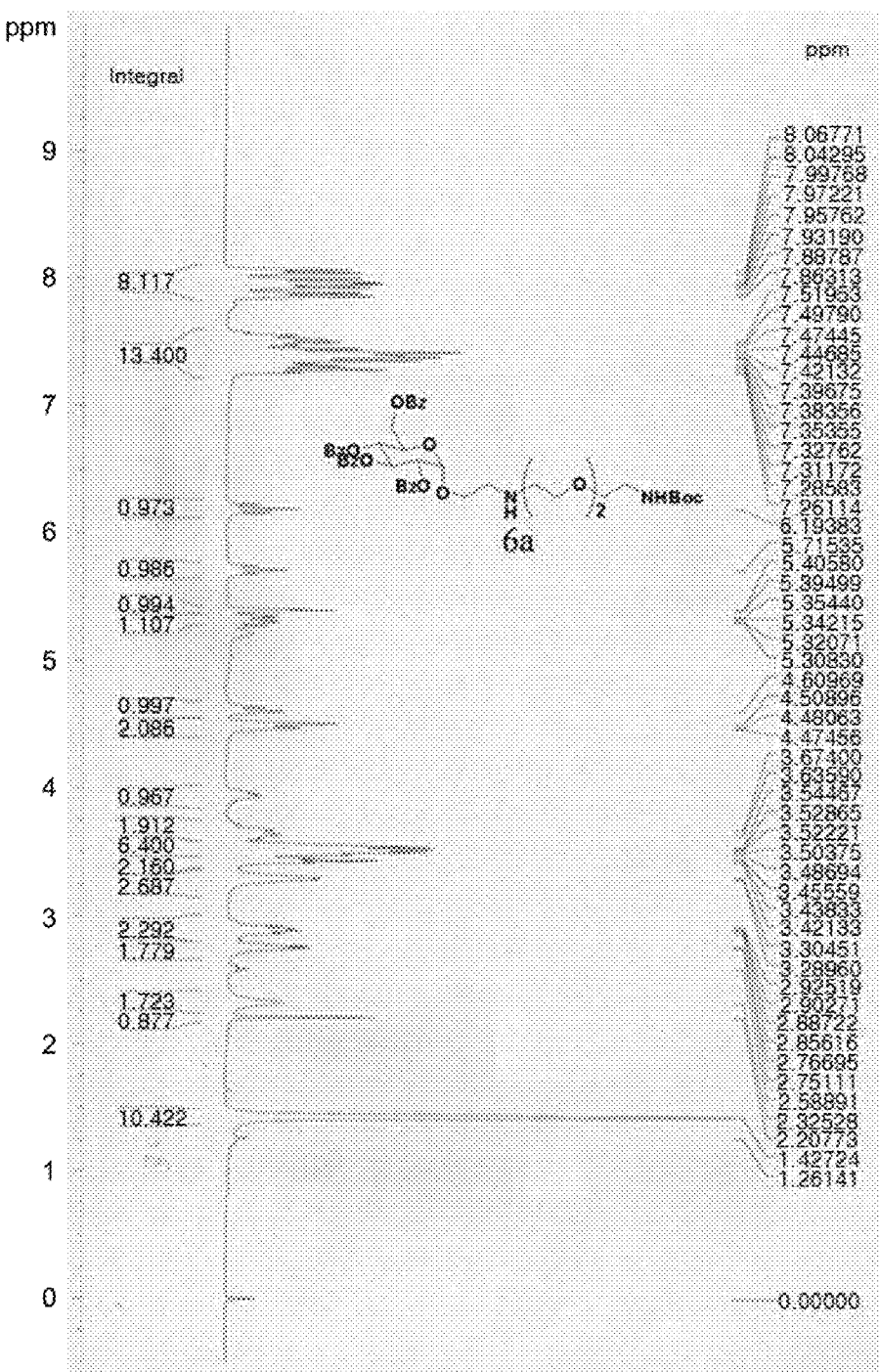
FIG. 5 illustrates $^1$H NMR data of a 2-(N-boc-3,6-dioxaoctane-1,8-diaminoethyl)]-2,3,4,6-tetra-O-benzoyl-α-D-glucoside (6a) compound that is an intermediate obtained in Example 1.
Figure 6:
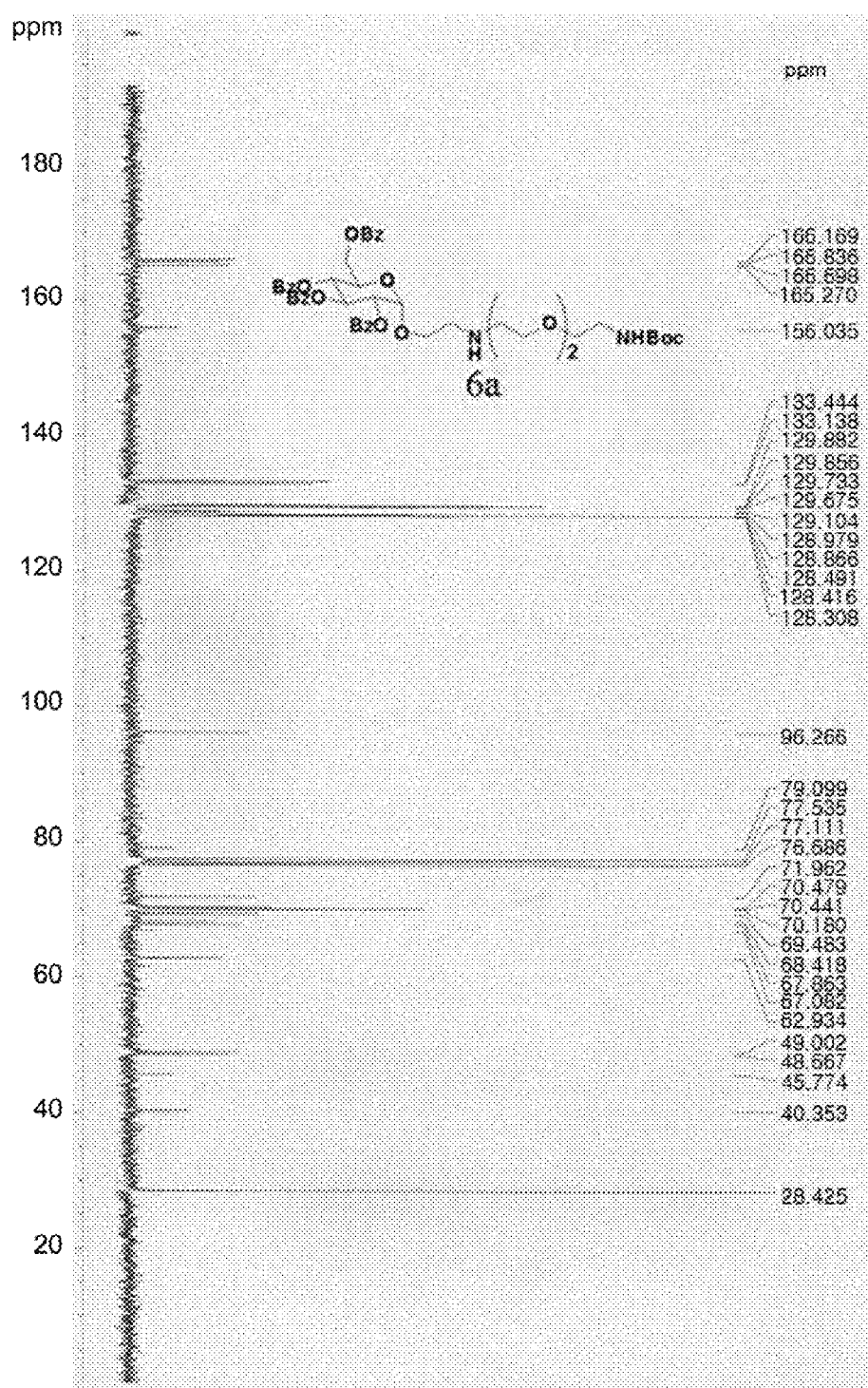
FIG. 6 illustrates $^{13}$C NMR data of a 2-(N-boc-3,6-dioxaoctane-1,8-diaminoethyl)]-2,3,4,6-tetra-O-benzoyl-α-D-glucoside (6a) compound that is an intermediate obtained in Example 1.
Figure 7:
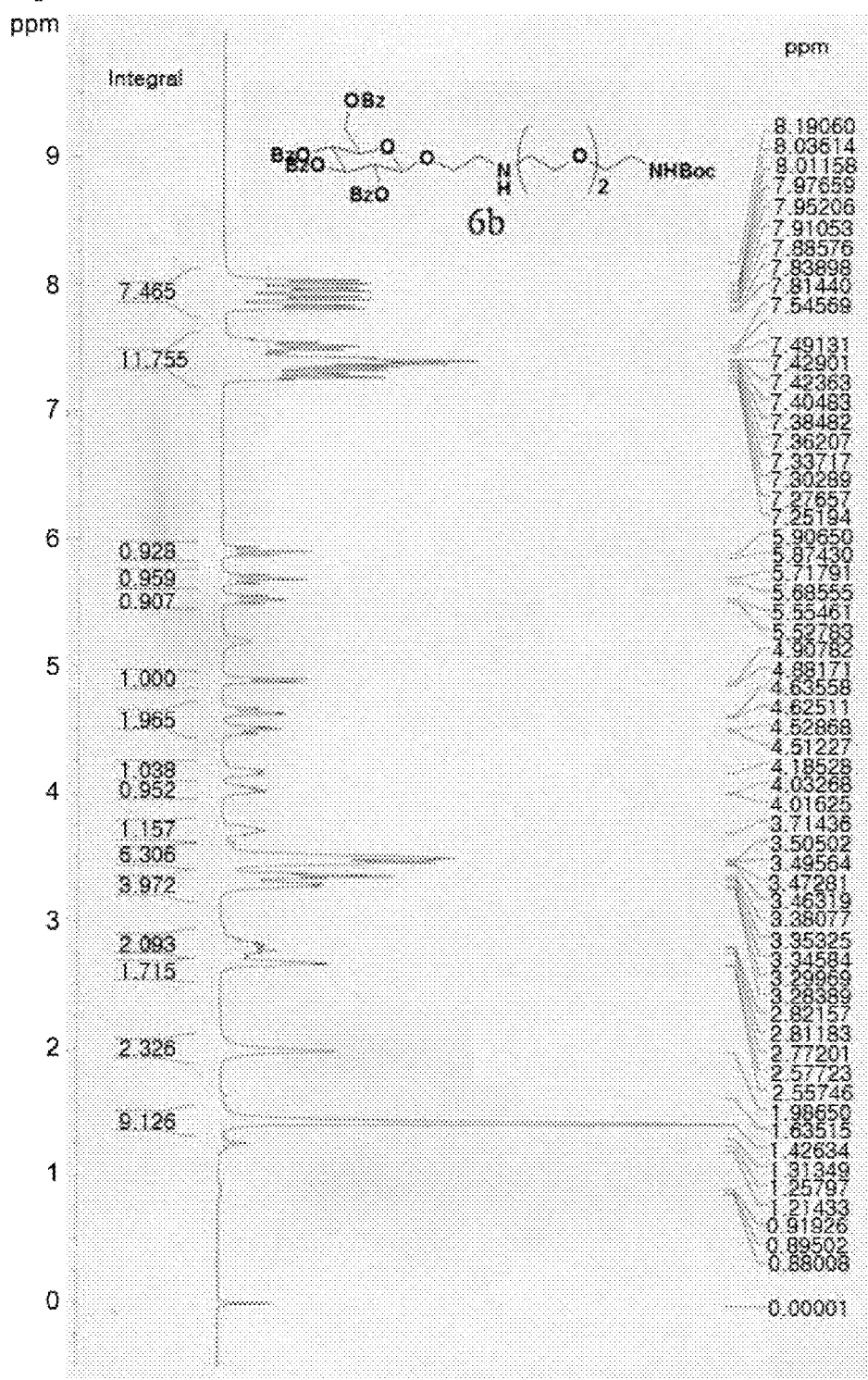
FIG. 7 illustrates $^1$H NMR data of a 2-(N-boc-3,6-dioxaoctane-1,8-diaminoethyl)]-2,3,4,6-tetra-O-benzoyl-β-D-glucoside (6b) compound that is an intermediate obtained in Example 1.
Figure 8:
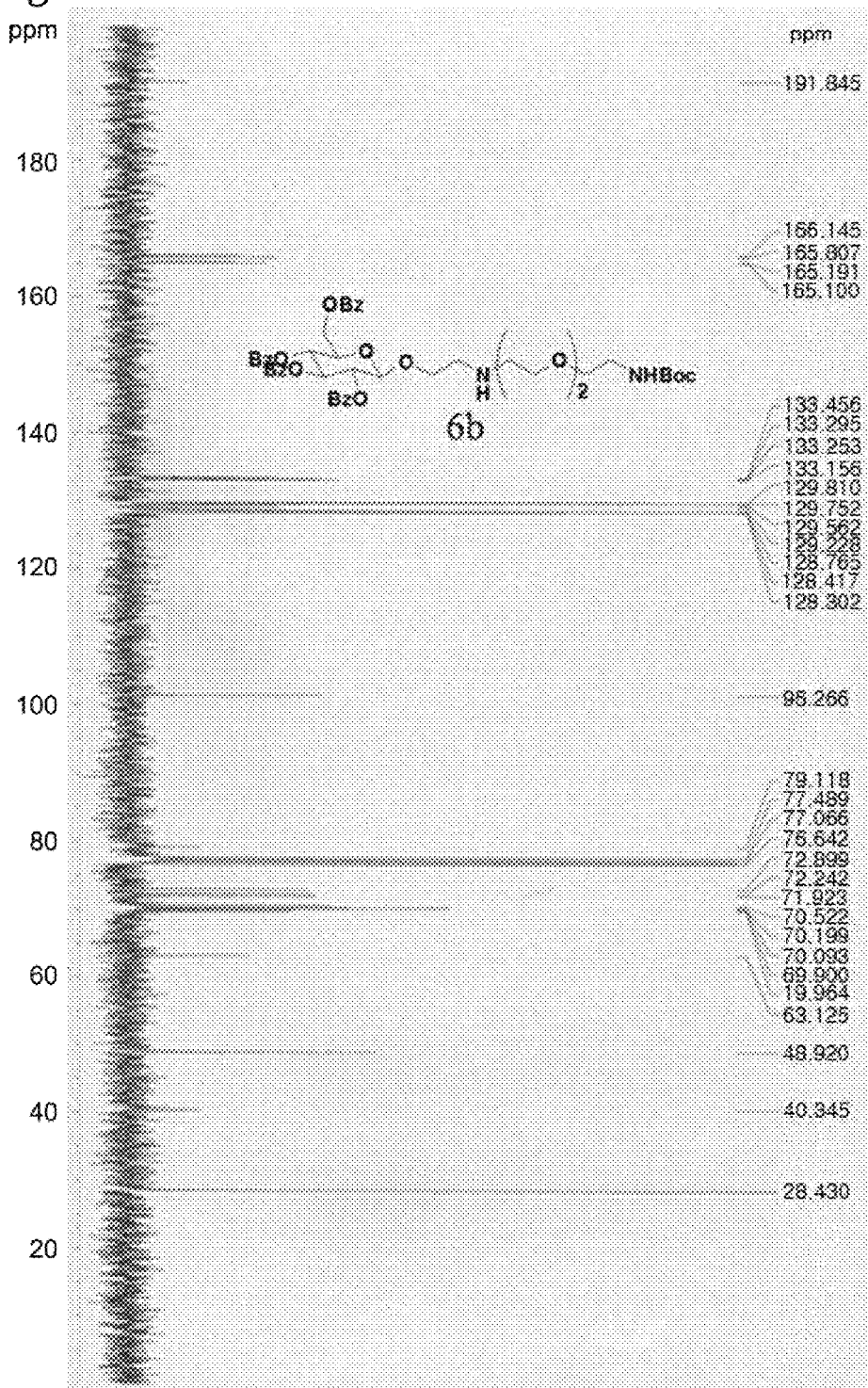
FIG. 8 illustrates $^{13}$C NMR data of a 2-(N-boc-3,6-dioxaoctane-1,8-diaminoethyl)]-2,3,4,6-tetra-O-benzoyl-β-D-glucoside (6b) compound that is an intermediate obtained in Example 1.
Figure 9:
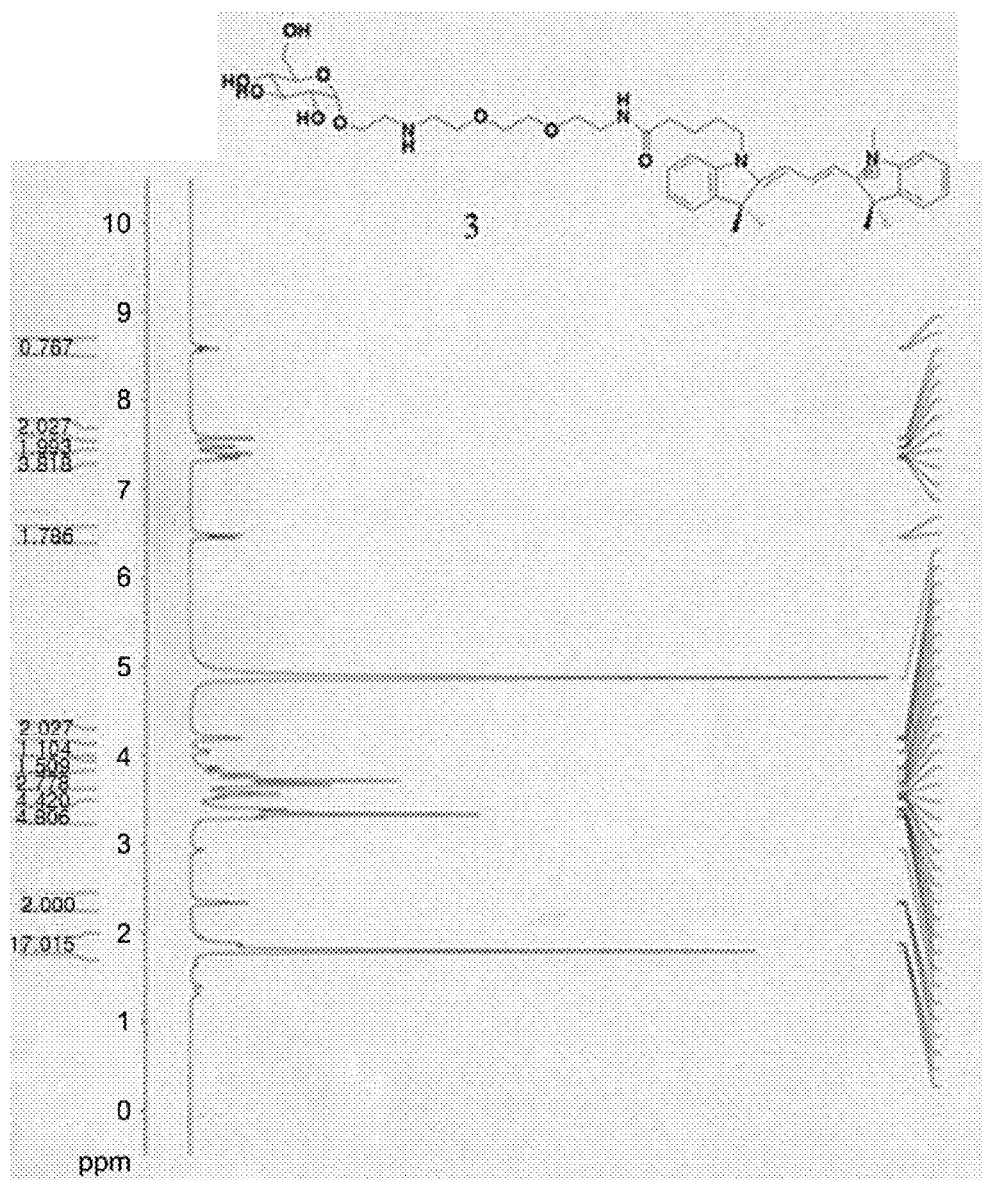
FIG. 9 illustrates $^1$H NMR data of [2-(N-Cy3-3,6-dioxaoctane-1,8-diaminoethyl)]-α-D-glucose (3) that is a final product obtained in Example 1.
Figure 10:
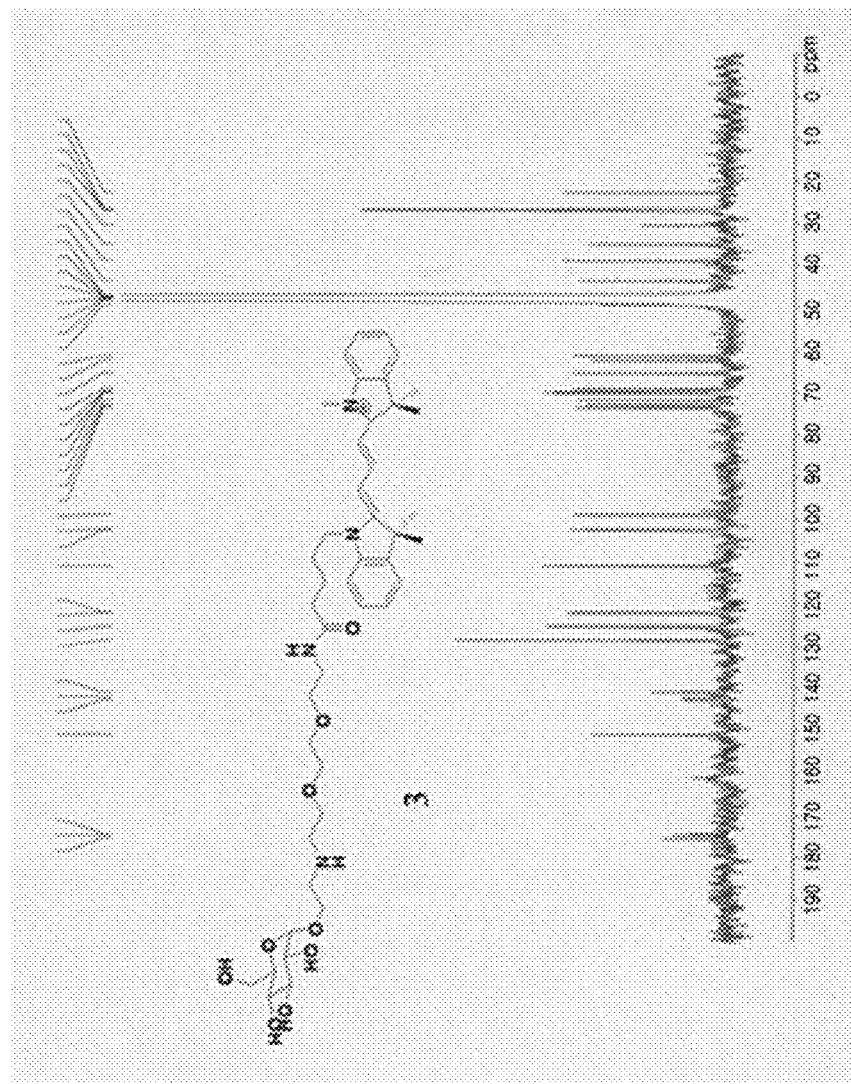
FIG. 10 illustrates $^{13}$C NMR data of [2-(N-Cy3-3,6-dioxaoctane-1,8-diaminoethyl)]-α-D-glucose (3) that is a final product obtained in Example 1.
Figure 11:
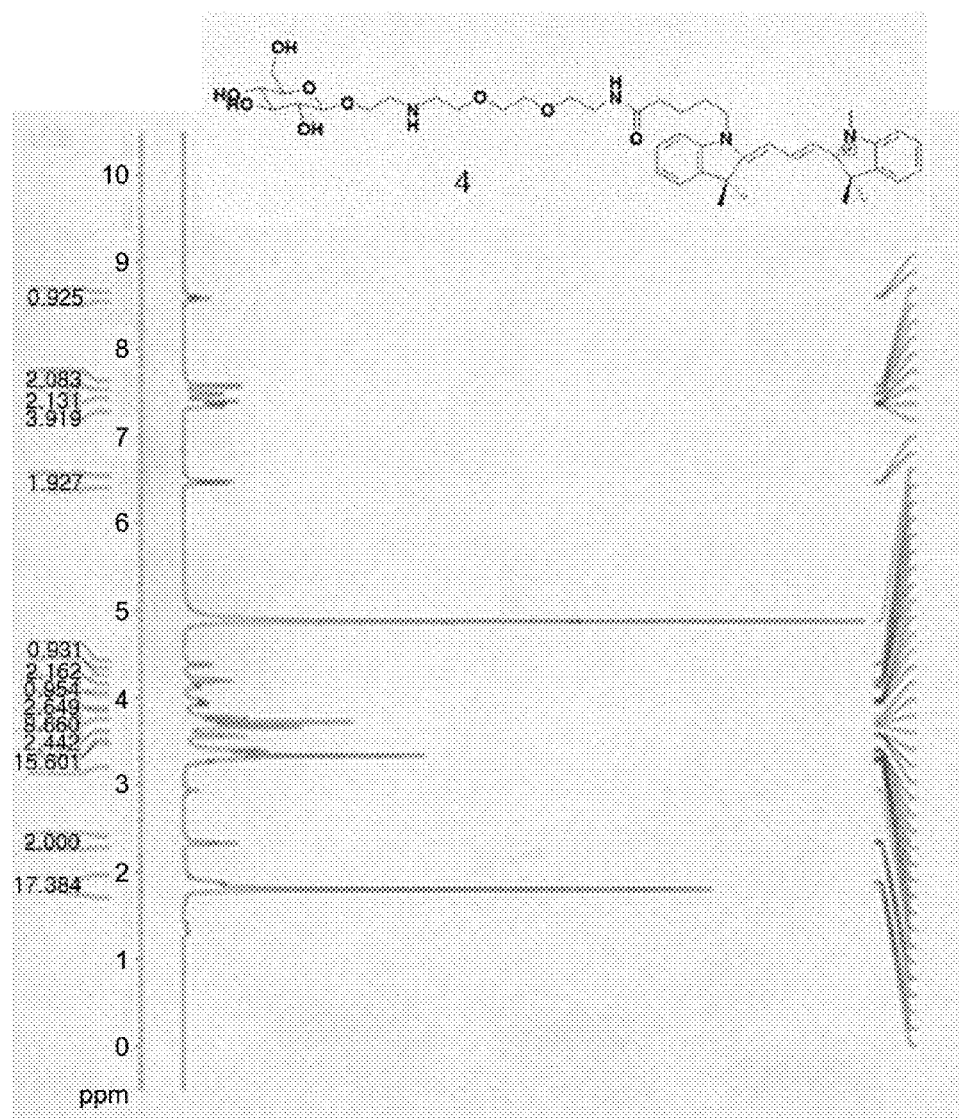
FIG. 11 illustrates $^1$H NMR data of (2-[(N-Cy3-3,6-dioxaoctane-1,8-diaminoethyl)]-β-D-glucose (4) that is a final product obtained in Example 1.
Figure 12:
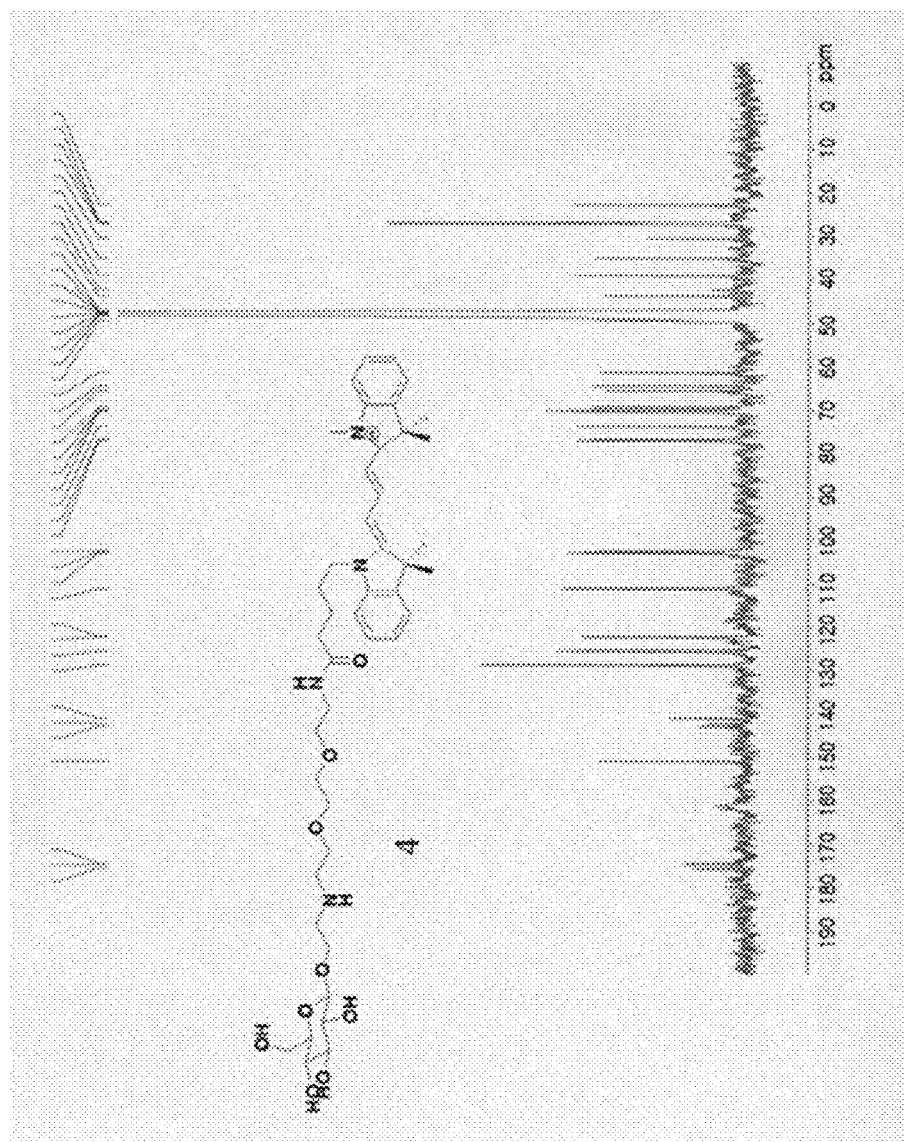
FIG. 12 illustrates $^{13}$C NMR data of [2-(N-Cy3-3,6-dioxaoctane-1,8-diaminoethyl)]-β-D-glucose (4) that is a final product obtained in Example 1.

In accordance with an aspect thereof, the present invention provides a fluorescent glucose analogue labeled with fluorescent dye by O-1-glycosylation and via various linkers including aliphatic, aromatic and heterocyclic rings.

In accordance with another aspect thereof, the present invention provides a method for the asymmetric synthesis of the fluorescent glucose analogue.

In accordance with a further aspect thereof, the present invention provides a bioprobe comprising the fluorescent glucose analogue.

In accordance with still a further aspect thereof, the present invention provides a molecular bioimaging method using the fluorescent glucose analogue as a bioprobe.

In accordance with still another aspect thereof, the present invention provides a FACS (fluorescent activated cell sorting) method using the fluorescent glucose analogue as a bioprobe.

In accordance with still yet another aspect thereof, the present invention provides a method for screening curative or preventive drugs of glucose metabolism-related diseases, using the fluorescent glucose analogue as a bioprobe.

Hereinafter, the present invention will be described in detail.

Specifically, the fluorescent glucose analogue of the present invention is represented by the following Formula 1 or Formula 2:

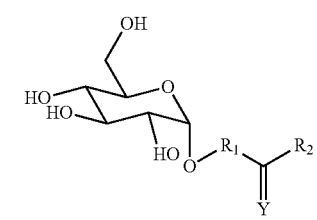
[Formula 1]

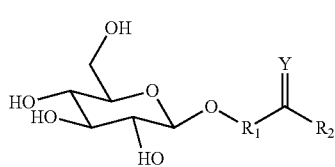
[Formula 2]

wherein $R_1$ is —$(CH_2)_n$—NH—, —$(CH_2)_n$—NH—$(C_2H_4X)_m$—NH—, —$(CH_2)_n$-A- or —$(CH_2)_n$—NH—$(CH_2)_{x1}$—B—$(CH_2)_{x2}$—NH— wherein n is an integer of from 1 to 10, m is an integer of from 1 to 100, and x1 and x2 may be the same or different and are an integer of from 0 to 10;

X is $CH_2$, O or a single bond, with the proviso that when m is 2 or more, Xs may be the same or different;

A is heterocycloalkylene of C2-C20 or heteroarylene of C2-C20, containing at least one heteroatom selected from among nitrogen, oxygen and sulfur therein;

B is cycloalkylene of C3-C20 or arylene of C6-C20;

$R_2$ is a fluorescent dye or a low-molecular weight organic compound capable of selectively binding to a fluorescent dye-labeled substance; and Y is O or S.

Examples of the fluorescent dye useful in the glucose analogue of the present invention include Cy3, Cy5, fluorescein isothiocyanate (FITC), tetramethylrhodamine isothiocyanate (RITC), Alexa, 4,4-difluoro-4-boro-3a,4a-diaza-s-indacene (BODIPY), Texas Red, and the two-photon dye 2-acetyl-6-dimethylaminonaphthalene (Acedan), but are not limited thereto. Selection may be made of avidin or streptavidin for the fluorescent dye-labeled substance and biotin for the low-molecular weight organic compound, but the present invention is not limited thereto.

In the context of the present invention, avidin or streptavidin may be labeled with a fluorescent dye by an immobilization means known in the art (e.g., a linker) or a chemical bond between functional groups thereof.

The glucose analogue of Formula 1 is an α anomer, while the glucose analogue of Formula 2 is a β anomer.

In the chemical formulas, heteroatoms such as nitrogen, oxygen, sulfur may be contained one or more in a ring. Two or more of the same or different heteroatoms (e.g., nitrogen atom and oxygen atom) may be contained in one ring.

In the chemical formulas, preferably, $R_1$ is —$(CH_2)_n$-A- wherein A is a heterocycloalkylene of C2-C20 containing therein one or more nitrogen atoms or oxygen atoms.

In the chemical formulas, more preferably, $R_1$ is

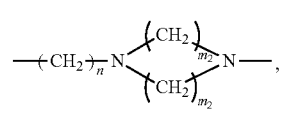

wherein n, $m_1$ and $m_2$ are independently an integer of from 1 to 10, $m_1$ and $m_2$ being the same or different.

In the chemical formulas, far more preferably, $R_1$ is —$(CH_2)_{x1}$—NH—$(CH_2)_{x2}$—B—NH— wherein B is a cycloalkylene of C3-C20 or an arylene of C6-C20, and x1 and x2 may be the same or different, being an integer of from 0 to 10.

More specifically, the glucose analogue of the present invention may be represented by one of the following Chemical Formulas 3 to 7:

[Chemical Formula 3]
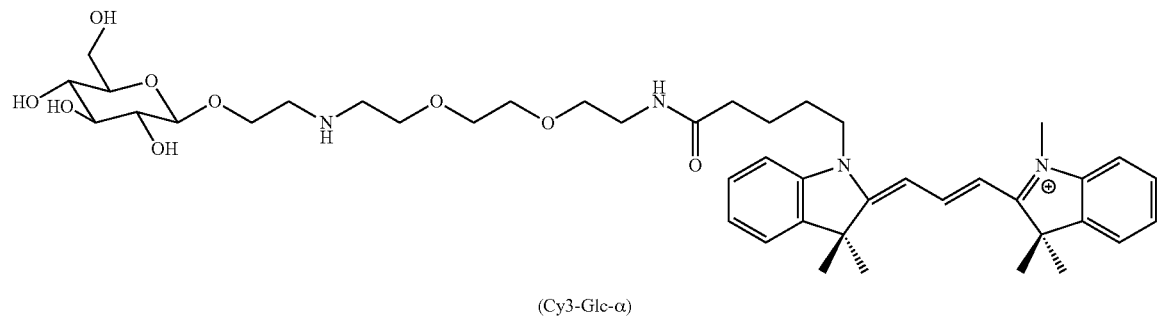
(Cy3-Glc-α)
[Chemical Formula 4]
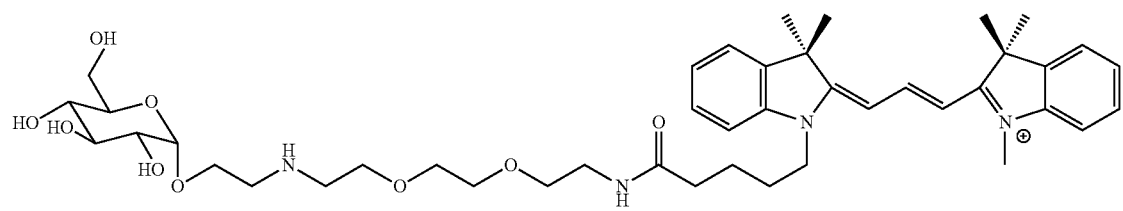
[Chemical Formula 5]
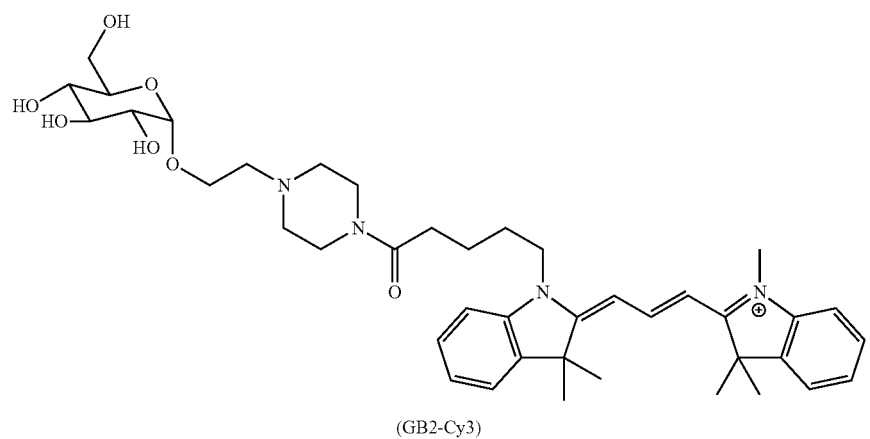
(GB2-Cy3)
[Chemical Formula 6]
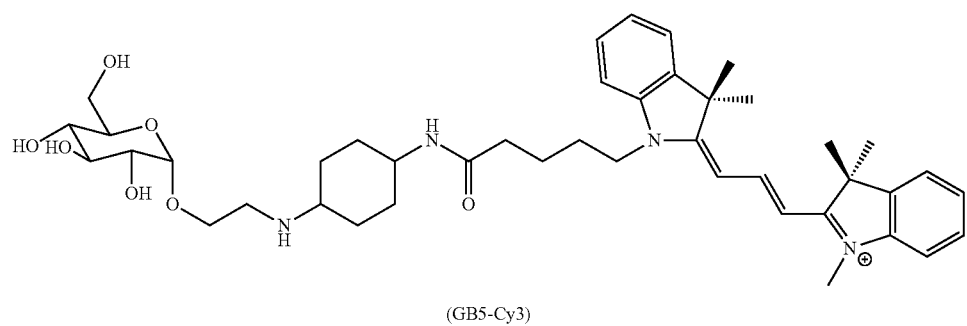
(GB5-Cy3)

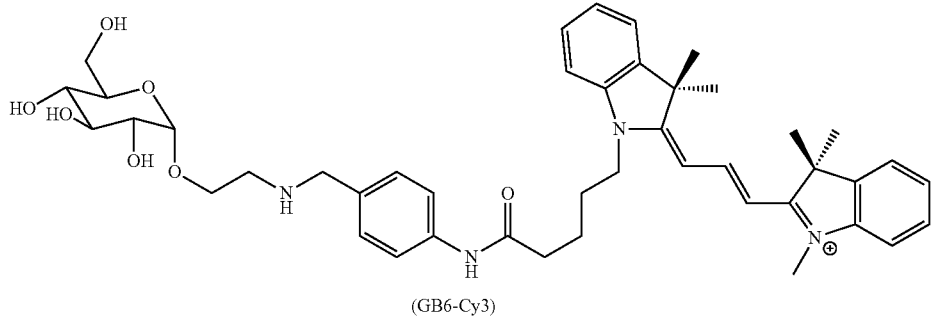

[Chemical Formula 7]

(GB6-Cy3)

The fluorescent glucose analogue may be synthesized by labeling glucose with fluorescent dye by O-1-glycosylation at the C-1 anomeric carbon position. For instance, the fluorescent glucose analogue may be prepared according to a method comprising:

(a) dissolving glucose (D-glucose), together with an ion exchange resin, in 2-bromoethanol with reflux at 50 to 80° C. to selectively introduce 2-bromoethanol into the carbon atoms of α and β anomeric positions;

(b) protecting the resulting reactants of step (a) with benzoyl group in pyridine, followed by separation into α and β anomers by column chromatography;

(c) reacting the resulting benzoyl group-protected α or β anomer of step (b) with a Boc group-containing compound in an organic solvent at 40 to 80° C., followed by purification; and (d) deprotecting the purified product of step (c), basifying the deprotected product and reacting with a fluorescent dye solution, followed by purification to afford a fluorescent glucose analogue represented by Chemical Formula 1 or 2.

This method makes it possible to asymmetrically synthesize glucose analogues in the form of the alpha anomer of Chemical Formula 1 and the beta anomer of Chemical Formula 2 at the same time.

A detailed description will be given of each step of the synthesis method below.

Step a

The conformation of D-glucose is recognized to be pyranose, which is hemiacetal. Due to the special reactivity of the anomeric hydroxyl group, 2-bromoethanol can be regioselectively introduced into the anomeric position by acid-catalyzed Fischer glycosylation with a 2:1 (α:β) ratio.

Accordingly, first, after D-glucose is dissolved in 2-bromoethanol in conjunction with the ion exchange resin, the reflux is performed at a temperature in the range of 50 to 70° C., and preferably 60 to 80° C., to regioselectively introduce 2-bromoethanol into the α and β anomeric positions. In connection with this, the ratio of α and β may be obtained by using nuclear magnetic resonance spectroscopy (NMR) [F. Fazio, M. C. Bryan, O. Blixt, J. C. Paulson, C.-H. Wong, *J. Am. Chem. Soc,* 2002, 124, 14397-14402].

Optionally, the obtained reaction mixture is filtered to remove the ion exchange resin and then concentrated in vacuo, and the glycosylated compound is purified by using column chromatography. In connection with this, the column chromatography may be, for example, a silica-gel flash column chromatography (ethyl acetate:methanol=10:1 to 5:1).

Step b

Subsequently, the reactants obtained in step a are reacted with, for example, halogenated benzoyl such as benzoyl chloride in pyridine to achieve the protection by a benzoyl group and then separate them into the α and β anomers by using column chromatography. In connection with this, the α anomer and the β anomer may be separated at the ratio of 2:1.

Preferably, after the reactants are protected by the benzoyl group and before the column chromatography is performed, the mixture was quenched with the addition of alkyl alcohol (for example, methyl alcohol) and the mixture was diluted, preferably with ethyl acetate followed by washing, drying, filtering, and condensing under reduced pressure of the organic layer.

In connection with this, a typical column chromatography may be used, and preferably the silica-gel flash column chromatography (ethyl acetate:n-hexane=1:3) may be used.

Step c

Subsequently, the α and β anomers that are protected by using the benzoyl group obtained in step b are reacted with compounds containing Boc groups in an organic solvent at a temperature in the range of 40 to 80° C., preferably 40 to 50° C. for the compounds of Chemical Formulas 3 and 4, and 70 to 80° C. for the compounds of Chemical Formulas 5 to 7, and then perform purification by using column chromatography.

In connection with this, it is preferable that before purifying the reactants, the obtained solution is diluted (preferably, ddH$_2$O is used), extracted (preferably, ethyl acetate as used), washed (preferably, brine is used), and condensed under reduced pressure according to a typical method.

A typical organic solvent may be used as the above organic solvent. Preferably, the organic solvent is dimethyl formamide (DMF) and triethyl amine (TEA). The compound containing the Boc group includes an amine connection group and the Boc groups, and preferably N-Boc-3,6-dioxaoctane-1,8-diamine having the amine connection group. However, the compound is not limited thereto.

In connection with this, typical column chromatography may be used, and preferably the silica-gel flash column chromatography (chloroform:ethanol TEA=87:8:5) is used.

Step d

Finally, the product obtained in step c is deprotected, basified and then reacted with a fluorescent dye solution, followed by purification by a conventional technique, for example, HPLC, to afford the fluorescent dye-labeled glucose of Chemical Formula 1 or 2.

The deprotection of the product of Step C may be performed in the following two manners.

For the compounds of Chemical Formulas 3 and 4, removal is first made of the benzoyl group and then of the Boc group, followed by basification to allow reaction with a fluorescent dye solution. For the compound of Chemical Formulas 5 to 7, the Boc group is removed first. The deprotected compound is basified and reacted with a fluorescent dye solution after which the benzoyl group is removed.

The debenzoylation may be carried out by reacting sodium methoxide with the compound to be deprotected in methyl alcohol. In this context, sodium methoxide may be added to a solution of the compound in methyl alcohol.

The removal of the Boc group may be performed by adding a 50% solution of trifluoroacetic acid (TFA) in dichloromethane to the compound to be deprotected and purging with $N_2$ to give a concentrate.

Meanwhile, in order to remove the trifluoroacetic acid that remains in the reaction mixture after deprotection of the Boc group, the basification is performed. The basification may be performed by reacting a dimethylformamide (DMF) solution in which the deprotected compound is dissolved with diisopropylethylamine (DIPEA). Through the basification treatment, chiral glucoside having primary amine is obtained.

Examples of the fluorescent dye useful in the present invention include Cy3, Cy5, fluorescein isothiocyanate (FITC), tetramethylrhodamin isothiocyanate (RITC), Alexa, 4,4-difluoro-4-boro-3a,4a-diaza-s-indacen (BODIPY), Texas Red and the two-photon dye, with preference for Cy3 because of stability to high-density light sources such as a laser and the like and extensive application to various types of bioassay systems. Therefore, the fluorescent dye solution is preferably a solution of Cy3-COOH and the reaction agent, 1-(3-dimethylaminopropyl)-3-ethylcarbodiimide (EDC) or (7-azabonzotriazol-1-yloxy)tripyrrolidinophosphinium hexafluorophosphate (PyAOP) in dimethylformamide (DMF). Besides, an organic compound such as biotin, or an inorganic compound such as nanoparticles may be employed according to the usage. Although biotin itself is not fluorescent, it may be used as a mediator of fluorescence in conjugation with fluorescent-labeled avidin or streptavidin that can bind thereto with high selectivity.

A glucose moiety is labeled with fluorescent dye such as Cy3 at C-1 anomeric position of glucoside through an amide bond with EDC, and subsequent HPLC allows the separation of the fluorescent dye-labeled glucose analogue according to the present invention. The final products may be completely identified using $^1H$, $^{13}C$ NMR, MALDI-TOF mass spectrometry, high resolution mass spectrometry or the like.

Acting as an analogue of D-glucose, the fluorescent glucose analogue prepared according to the synthesis method of the present invention competes with D-glucose in a time- and dose-dependent manner for intracellular uptake whereas L-glucose has no influences on the intracellular uptake of the fluorescent glucose analogue of the present invention. In addition, the fluorescent glucose analogue of the present invention is observed to have higher uptake into glucose metabolism-enhanced cells such as cancer cells, e.g., lung cancer, melanoma, etc., than normal cells, which indicates that the fluorescent glucose analogue of the present invention is transported into cells by a glucose-specific transport system (e.g., GLUT4) and that the fluorescent glucose analogue of the present invention can be used as a means for glucose metabolism monitoring.

The compound of Chemical Formula 1, e.g., the compound of Chemical Formula 3 or 5, shows a higher performance as a glucose uptake probe than does the known compound of the following Formula 8, that is, 2-NBDG, which can be obtained by the N-2-glycosylation of the fluorescent dye NBD.

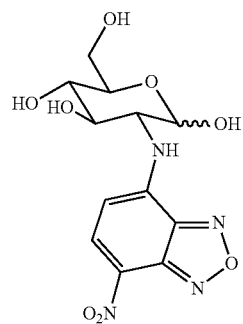

[Formula 8]

2-NBDG, a conventional fluorescent glucose analogue, is little detected even at as high a concentration as 125 μM. On the other hand, as low as 12.5 μM of the fluorescent glucose analogue of Chemical Formula 3 (Cy3-Glc-α) is sufficient for the detection thereof. The fluorescent glucose analogue of Chemical Formula 5 (GB2-Cy3) is found to compete even at as low a concentration as 5 μM with D-glucose for cellular uptake.

Also, the cellular uptake of the compound of Chemical Formula 5 (GB2-Cy3) greatly fluctuates according to glucose concentration, so that it can be used for sensitively monitoring the cellular uptake of glucose. Further, 3T3/L1 preadipocytes into which the compound of Chemical Formula 5 was introduced were found to increase in fluorescence intensity with the advance of differentiation, as measured by flow cytometry. Thus, the compound can be used as a probe for monitoring the differentiation of 3T3/L1 cells into mature adipocytes. Moreover, the use of the compound of Chemical Formula 5 (GB2-Cy3) as a probe demonstrated the enhanced cellular uptake of glucose under insulin- and AICAR-stimulated conditions in both 3T3/L1 adipocytes and C2C12 muscle cells, and the effectively reduced cellular uptake of glucose under the treatment with dexamethasone.

Therefore, the fluorescent glucose analogue provided by the present invention may act as a bioprobe and be efficiently applied to bioimaging, molecular bioimaging, bioassay, novel medicine screening or the like.

In particular, the fluorescent glucose analogue according to the present invention may be applied to cancer or tumor imaging or molecular bioimaging for studies on glucose transporters-related cell metabolism.

In this regard, a confocal laser scanning microscope (CLSM), an inverted fluorescent microscope, a fluorescent activated cell sorter (FACS), a microplate reader, a high content screening and the like may be used in the molecular bioimaging method.

In addition, the fluorescent glucose analogue of the present invention may be used as a bioprobe in screening therapeutics and preventives for glucose metabolism-related diseases by FACS (Fluorescence Activated Cell Sorting). FACSCalibur™ (BD BioScience) may be suitable as a flow cytometer. This apparatus may allow accurate quantitative analysis which is difficult to achieve with molecular bioimaging.

When employing the conventional glucose analogue 2-NBDG (50 μM), cells in 11 mM glucose-containing media were found to differ in fluorescence intensity from those in glucose-depleted media by 30% reduction, as measured by FACS. On the other hand, it was observed through the difference of fluorescence intensity that the cellular uptake of the fluorescent glucose analogue of the present invention (5 μM) in 11 mM glucose-containing media was reduced by about 60% than the cellular uptake in glucose-depleted media. That means the fluorescent glucose analogue of the present invention enters the cell through glucose transporter (GLUT) system via a competition with glucose in the media. Therefore, the fluorescent glucose analogue of the present invention can serve as a more sensitive probe for screening therapeutic and preventive drugs for glucose metabolism-related diseases, under a practical cellular environment, than can the conventional analogue.

For cellular uptake, the analogue may be used at a concentration of from 1 to 100 μM, preferably from 1 to 20 μM, and more preferably from 3 to 10 μM. It takes 40 min or less and preferably 25 to 35 min to culture cells to the maximal intracellular uptake of the probe.

In accordance with another aspect, the present invention provides a method for screening curative or preventive drugs for glucose metabolism-related disease, using the fluorescent glucose analogue as a bioprobe.

As described above, glucose metabolism is one of the most important metabolisms in living organisms. A problem with this metabolism may lead to various types of diseases. For example, cancer or tumors may result. Thus, the fluorescent glucose analogue of the present invention may be applied to a method for screening anti-cancer agents. Illustrative but non-limiting examples of the anti-cancer agents may preferably include curative or preventive agents for lung cancer, stomach cancer, liver cancer, or colon cancer.

The fluorescent glucose analogue according to the present invention has a high probability as a novel bioprobe used to screen an efficient novel biomedicines used to cure diseases directly related to glucose metabolism, that is, diabetes which is caused by inefficient glucose metabolism and/or uptake in cells, and obesity which is caused by the excessively active glucose metabolism. In an example for the screening method of the present invention, the fluorescent glucose analogue of the present invention is used as a probe when the intracellular uptake of glucose is analyzed after 3T3/L1 adipocytes and C2C12 myoblasts are treated with insulin and ATCAR. Hence, the fluorescent glucose analogue of the present invention can be used for screening diabetes therapeutics.

Therefore, the analogue according to the present invention may be used for evaluating the performance of substances which regulate physiological activities relevant to glucose metabolism and for screening drug candidates.

A better understanding of the present invention may be obtained in light of the following Examples which are set forth to illustrate, but are not to be construed as limiting the present invention.

EXAMPLE 1

Synthesis of [2-(N-Cy3-3,6-Dioxaoctane-1,8-diaminoethyl)]-α,β-D-glucose (Cy3-Glc-α,β)

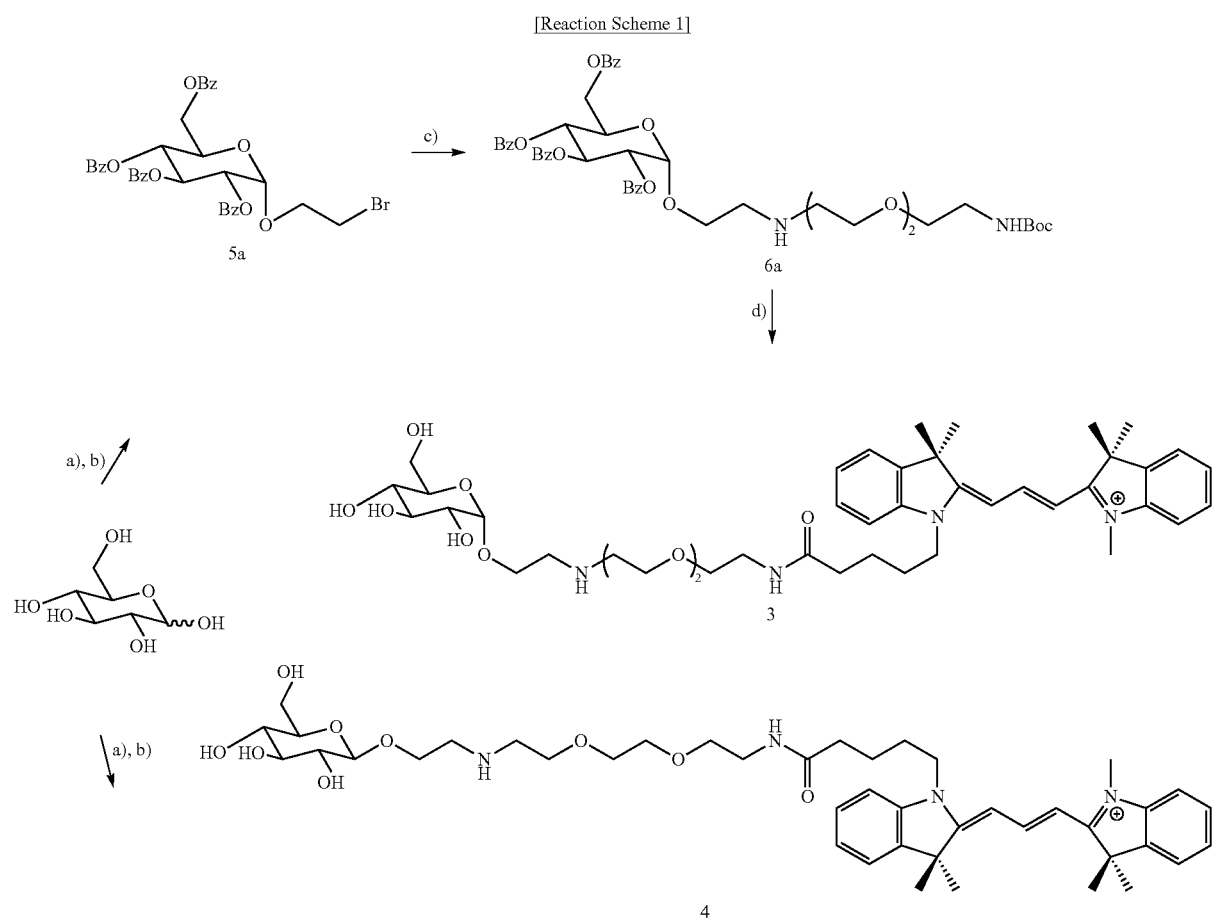

[Reaction Scheme 1]

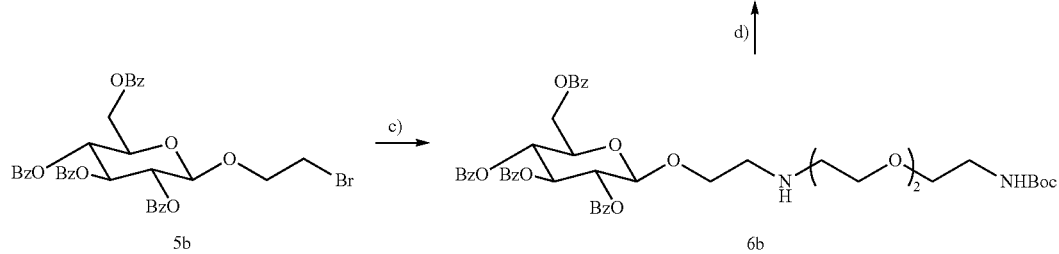

a) 2-bromoethanol, the Dowex 50WX8-400 ion exchange resin, 70° C. reflux; b) benzoyl chloride, pyridine, dimethyl aminopyridine (DMAP); c) N-Boc-3,6-dioxaoctane-1,8-diamine, triethylamine, dimethylformamide (DMF), 50° C.; d) (i) sodium methoxide (NaOMe), methanol; (ii) 50% trifluoroacetic acid (TFA)/dichloromethane (DCM); (iii) Cy3-COOH, EDC, diisopropylethylamine (DIPEA), dimethylformamide (DMF)

1. Preparation of (2-bromoethyl)-2,3,4,6-tetra-O-benzoyl-α-D-glucoside (5a) and (2-bromoethyl)-2,3,4,6-tetra-O-benzoyl-β-D-glucoside (5b)

Glucose (1 g, 5.55 mmol) was dissolved in 2-bromoethanol (6 mL, 85 mmol) with Dowex 50WX8-400 ion exchange resin. The reaction mixture was refluxed at 70° C. overnight and the reaction completion was monitored by TLC [F. Fazio, M. C. Bryan, O. Blixt, J. C. Paulson, C.-H. Wong, *J. Am. Chem. Soc,* 2002, 124, 14397-14402]. Subsequently, the reaction mixture was filtered to remove the resin and concentrated in vacuo. After the purification of glycosylated compound by silica-gel flash column chromatography (ethyl acetate:methanol=10:1 to 5:1), the desired compound was a mixture of α and β anomers in 2:1 ratio (total yield 74%) confirmed by nuclear magnetic resonance (NMR). The free hydroxyl groups on the resulting (2-bromoethyl)-D-glucoside (2.7 g, 9.5 mmol) were benzoylated in pyridine (60 mL) by drop-wise addition of benzoyl chloride (8.8 mL, 76 mmol) over 10 min at 0° C., followed by stirring at room temperature for overnight in the presence of dimethylaminopyridine (DMAP) (116 mg, 0.952 mmol) [a) M. A. Maier, C. G. Yannopoulos, N. Mohamed, A. Roland, H. Fritz, V. Mohan, G. Just, M. Manoharan, *Bioconjugate Chem.* 2003, 14, 1829; b) R. E. Campbell, M. E. Tanner, *J. Org. Chem.* 1999, 64, 9487-9492]. The mixture was quenched with the addition of methanol (10 mL) and the reaction mixture was diluted with ethyl acetate. The organic layer was washed with 1N hydrochloric acid (HCl) and sat. sodium bicarbonate (NaHCO₃), and dried over anhydrous magnesium sulfate (MgSO₄). Then, the organic layer was filtered and condensed under reduced pressure, and each of the desired anomers was successfully isolated by silica-gel flash column chromatography (ethyl acetate:n-hexane=1:3) in a 2:1 (α:β) ratio.

(1) α[(2-bromoethyl)-2,3,4,6-tetra-O-benzoyl-α-D-glucoside (5a)]: $^1$H NMR (300 MHz, CDCl$_3$) δ 8.09 7.89 (m, 8H), 7.54 7.31 (m, 12H), 6.23 (t, J=9.9 Hz, 1H), 5.70 (t, J=9.9 Hz, 1H), 5.44 (d, J=3.6 Hz, 1H), 5.33 (dd, J=10.1, 3.7 Hz, 1H), 4.64 4.56 (m, 2H), 4.48 (dd, J=11.9, 5.1 Hz, 1H), 4.16 4.03 (m, 1H), 3.94 3.85 (m, 1H), 3.76 3.70 (m, 2H); $^{13}$C NMR (75 MHz, CDCl$_3$) δ 166.20, 165.88, 165.78, 165.30, 133.48, 133.19, 129.98, 129.91, 129.76, 129.72, 129.63, 129.10, 128.93, 128.79, 128.45, 128.32, 96.31, 71.83, 70.30, 69.34, 68.92, 68.31, 62.95, 29.80; MALDI TOF MS calcd for C$_{36}$H$_{43}$O$_{12}$ [M+H]$^+$: 703.11; found: 703.05.

(2) β[(2-bromoethyl)-2,3,4,6-tetra-O-benzoyl-β-D-glucoside (5b)]: $^1$H NMR (300 MHz, CDCl$_3$) δ 8.04 7.81 (m, 8H), 7.44 7.28 (m, 12H), 5.91 (t, J=9.6 Hz, 1H), 5.67 (t, J=9.7 Hz, 1H), 5.54 (dd, J=7.9, 1.7 Hz, 1H), 4.93 (d, J=7.8 Hz, 1H), 4.66 (dd, J=9.1, 3.0 Hz, 1H), 4.48 (dd, J=6.8, 5.3 Hz, 1H), 4.24 4.07 (m, 2H), 3.94 3.83 (m, 1H), 3.49 3.36 (m, 2H); $^{13}$C NMR (75 MHz, CDCl$_3$) δ 165.15, 165.82, 165.22, 133.56, 133.34, 129.86, 129.78, 129.55, 129.26, 129.09, 128.75, 128.49, 128.40, 128.37, 128.29, 101.54, 72.81, 72.40, 71.69, 69.89, 69.64, 63.03, 29.74; MALDI TOF MS calcd for C$_{36}$H$_{43}$O$_{12}$ [M+H]$^+$: 703.11; found: 703.16.

Meanwhile, $^1$H NMR and $^{13}$C NMR data of the compounds 5a and 5b are shown in FIGS. 1 to 4.

2. Preparation of 2-(N-boc-3,6-dioxaoctane-1,8-diaminoethyl)]-2,3,4,6-tetra-O-benzoyl-α-D-glucoside (6a) and 2-(N-boc-3,6-dioxaoctane-1,8-diaminoethyl)]-2,3,4,6-tetra-O-benzoyl-β-D-glucoside (6b)

(1) 2-(N-boc-3,6-dioxaoctane-1,8-diaminoethyl)]-2,3,4,6-tetra-O-benzoyl-α-D-glucoside (6a)

To a solution of compound 5a (120 mg, 0.170 mmol) in 1 mL anhydrous DMF were added N-Boc-3,6-dioxaoctane-1,8-diamine [a) M. Trester-Zedlitz, K. Kamada, S. K. Burley, D. Fenyo, B. T. Chait, T. W. Muir, *J. Am. Chem. Soc.* 2003, 125, 2416-2425; b) Y. Li, Y.-M. Zhu, H.-J. Jiang, J.-P. Pan, G.-S. Wu, J.-M. Wu, Y.-L. Shi, J.-D. Yang, B.-A. Wu, *J. Med. Chem.* 2000, 43, 1635-1640] (127 mg, 0.512 mmol) and TEA (71 μL, 0.512 mmol), and the reaction mixture was stirred at 50° C. After the reaction completion was monitored by TLC, the resulting solution was diluted with ddH$_2$O, and then extracted with ethyl acetate. The combined organic layer was washed with brine, condensed under reduced pressure, and purified by silica-gel flash column chromatography (chloroform:ethanol:TEA=87:8:5) to obtain compound 6a as a yellowish oily compound (114 mg, 76%).

$^1$H NMR (300 MHz, CDCl$_3$) δ 8.06 7.86 (m, 8H), 7.52 7.28 (m, 12H), 6.19 (t, J=9.8 Hz, 1H), 5.71 (t, J=9.6 Hz, 1H), 5.40 (d, J=3.5 Hz, 1H), 5.33 (dd, J=10.1, 3.7 Hz, 1H), 4.62 (d, J=9.5 Hz, 1H), 4.50 4.47 (m, 2H), 3.99 3.94 (m, 1H), 3.72 3.60 (m, 2H), 3.54 3.50 (m, 6H), 3.44 (t, J=5.1 Hz, 2H), 3.29 (d, J=4.5 Hz, 2H), 2.92 2.86 (m, 2H), 2.78 2.73 (m, 2H), 2.32 (s, 2H), 2.20 (s, 1H), 1.42 (s, 9H); $^{13}$C NMR (75 MHz, CDCl$_3$) δ 166.17, 165.83, 165.69, 165.27, 156.03, 133.44, 133.13, 129.88, 129.85, 129.73, 129.67, 129.10, 128.97, 128.86, 128.49, 128.41, 128.30, 96.26, 79.09, 71.96, 70.47, 70.44, 70.18, 69.48, 68.41, 67.86, 67.08, 62.93, 49.00; 48.66, 40.35, 28.42; MALDI TOF MS calcd for C$_{47}$H$_{55}$N$_2$O$_{14}$ [M+H]$^+$: 871.36; found: 871.51

(2) 2-(N-boc-3,6-dioxaoctane-1,8-diaminoethyl)]-2,3,4,6-tetra-O-benzoyl-β-D-glucoside (6b)

The same procedure, except using compound 5b instead of compound 5a, was performed to obtain compound 6b (104 mg, 70%).

¹H NMR (300 MHz, CDCl₃) δ8.197.81 (m, 8H), 7.547.25 (m, 12H), 5.90 (t, J=9.6 Hz, 1H), 5.68 (t, J=9.7 Hz, 1H), 5.52 (t, J=8.0 Hz, 1H), 4.89 (d, J=7.8 Hz, 1H), 4.65 (dd, J=12.1, 2.9 Hz, 1H), 4.50 (dd, J=12.1, 4.9 Hz, 1H), 4.184.15 (m, 1H), 4.064.00 (m, 1H), 3.753.68 (m, 1H), 3.503.46 (m, 6H), 3.36 (t, J=5.2 Hz, 2H), 3.29 (d, J=4.7 Hz, 2H), 2.822.66 (m, 4H), 1.98 (s, 2H), 1.42 (s, 9H) ¹³C NMR (75 MHz, CDCl₃) δ191.84, 166.14, 165.80, 165.19, 165.10, 133.45, 133.29, 133.25, 133.15, 129.81, 129.75, 129.56, 129.22, 128.76, 128.41, 128.30, 101.43, 79.11, 72.89, 72.24, 71.92, 70.52, 70.19, 70.09, 69.90, 69.69, 63.12, 48.92, 40.34, 28.43; MALDI TOF MS calcd for $C_{47}H_{55}N_2O_{14}$ [M+H]⁺: 871.36; found: 871.59

Meanwhile, ¹H NMR and ¹³C NMR data of the compounds 6a and 6b are shown in FIGS. 5 to 8.

3. Preparation of [2-(N-Cy3-3,6-dioxaoctane-1,8-diaminoethyl)]-α-D-glucose (3) and [2-(N-Cy3-3,6-dioxaoctane-1,8-diaminoethyl)]-β-D-glucose (4)

(1) [2-(N-Cy3-3,6-dioxaoctane-1,8-diaminoethyl)]-α-D-glucose (3)

To a solution of compound 6a (20 mg, 0.023 mmol) in 1 mL of methanol was added sodium methoxide (0.5 M in methanol, 368 μL, 0.184 mmol) for debenzoylation of compound 6a. After the reaction, was completed, the mixture was neutralized with methanolic HCl, and then concentrated in vacuo. For the deprotection of Boc group on primary amine, a solution of 50% TFA in dichloromethane was added to the residue, followed by concentration by N₂ purging. The resulting fully deprotected compound in DMF (300 μL) was basified with DIPEA and added with Cy3-OH (10 mg, 0.022 mmol) and EDC (7 mg, 0.046 mmol) in 50 μL DMF. The reaction mixture was stirred at room temperature and the reaction was monitored by HPLC analysis. The elution protocol for analytical HPLC starts with 95% water and 5% acetonitrile for 5 min, followed by a linear gradient to 5% water and 95% acetonitrile over 35 min, continued to a linear gradient to 0% water and 100% acetonitrile over 5 min, held at 0% water and 100% acetonitrile for 15 min, and finally returned to 95% water and 5% acetonitrile over 10 min. Purification by prep HPLC affords 5.2 mg (30%) of the desired compound 3 (retention time: 25 min). The desired product was confirmed by ¹H, ¹³C NMR, MALDI-TOF MS, and HRMS.

¹H-NMR (500 MHz, MeOD) δ8.55 (t, J=13 Hz, 1H), 7.54 (d, J=7.5 Hz, 2H), 7.45 (q, J=7 Hz, 2H), 7.377.29 (m, 5H), 6.43 (d, J=13.5 Hz, 2H), 4.16 (t, J=7.5 Hz, 2H), 4.033.99 (m, 1H), 3.82 (dd, J=11.5, 2.0 Hz, 1H), 3.75 (t, J=4.5 Hz, 2H), 3.69 (s, 5H), 3.663.59 (m, 7H), 3.53 (t, J=6.0 Hz, 3H), 3.48 (dd, J=9.5, 3.5 Hz, 1H), 3.36 (t, J=6.0 Hz, 4H), 3.283.26 (m, 4H), 2.30 (t, J=7.0 Hz, 2H), 1.80 (s, 17H); ¹³C NMR (125 MHz, MeOD) δ175.56, 174.77, 174.36, 150.96, 142.84, 142.13, 140.97, 128.77, 125.61, 125.52, 122.33, 122.17, 111.17, 111.00, 102.60, 102.39, 99.05, 73.71, 73.11, 72.03, 70.35, 70.20, 70.01, 69.35, 65.63, 62.48, 61.43, 49.42, 43.71, 38.98, 35.04, 30.55, 27.11, 26.93, 26.73, 22.79; HRMS (FAB+): calcd for $C_{43}H_{63}N_4O_9$ [M]⁺: 779.4595; found, 779.4601.

(2) (2-(N-Cy3-3,6-dioxaoctane-1,8-diaminoethyl)]-β-D-glucose (4)

The same procedure was performed except compound 6b was used instead of compound 6a, to obtain compound 4 (7.6 mg, 42%).

¹H NMR (500 MHz, MeOD) δ8.58 (t, J=13.5 Hz, 1H), 7.57 (d, J=7.0 Hz, 2H), 7.48 (d, J=4.5 Hz, 2H), 7.397.34 (m, 4H), 6.46 (d, J=13.5 Hz, 2H), 4.38 (d, J=7.5 Hz, 1H), 4.19 (t, J=7.0 Hz, 2H), 4.144.11 (m, 1H), 3.973.91 (m, 2H), 3.77 (t, J=5.0 Hz, 2H), 3.723.66 (m, 9H), 3.56 (t, J=5.5 Hz, 2H), 3.403.24 (m, 11H), 2.33 (t, J-6.5 Hz, 2H), 1.79 (s, 17H); 13C NMR (125 MHz, MeOD) δ175.56, 174.77, 174.36, 150.96, 142.83, 142.13, 140.97, 128.78, 125.62, 125.53, 122.33, 122.17, 111.18, 111.09, 102.97, 102.61, 102.39, 77.02, 76.71, 73.69, 70.33, 70.16, 70.01, 69.36, 65.53, 64.49, 61.36, 49.42, 43.71, 38.97, 35.05, 30.51, 27.11, 26.93, 26.73, 22.79; HRMS (FAB⁺) calcd for $C_{43}H_{63}N_4O_9$ [M]⁺: 779.4589; found, 779.4609.

Meanwhile, ¹H NMR and ¹³C NMR data of compounds 3 and 4 are shown in FIGS. 9 to 12.

EXAMPLE 2

Synthesis of [2-(N-Cy3-piperazinoethyl)]-α-D-glucose (GB2-Cy3)

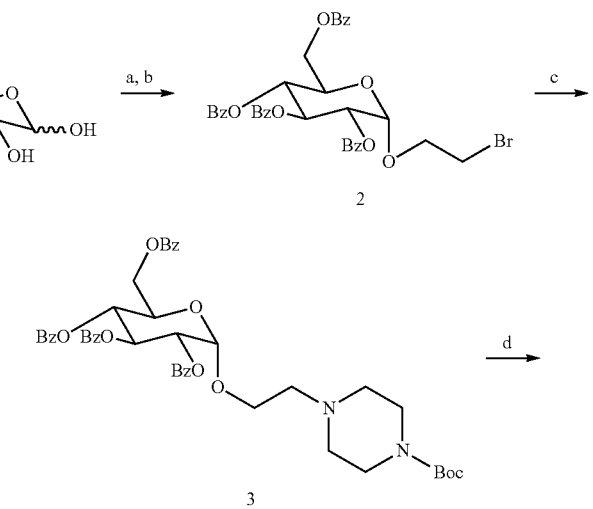

[Reaction Scheme 2]

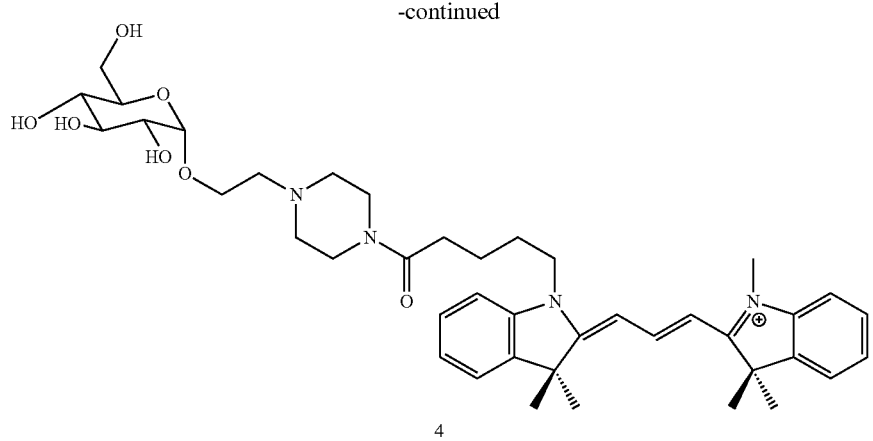

4 a) 2-bromoethanol, the Dowex 50WX8-400 ion exchange resin, 70° C. reflux; b) benzoyl chloride, pyridine, dimethyl aminopyridine (DMAP); c) N-Boc-piperazine, triethylamine, dimethylformamide (DMF), 80° C.; d) (i) 50% trifluoroacetic acid (TFA), dichloromethane (DCM); (ii) Cy3-COOH, EDC (a coupling reagent, such as PyAOP and PyBOP, may be used instead), diisopropylethylamine (DIPEA), dimethylformamide (DMF); (iii) sodium methoxide (NaOMe), methanol

1. Preparation of (2-bromoethyl)-2,3,4,6-tetra-O-benzoyl-α-D-glucoside (2)

Glucose (1 g, 5.55 mmol) was dissolved in 2-bromoethanol (6 mL, 85 mmol) with Dowex 50WX8-400 ion exchange resin. The reaction mixture was refluxed at 70° C. overnight and the reaction completion was monitored by TLC [F. Fazio, M. C. Bryan, O. Blixt, J. C. Paulson, C.-H. Wong, *J. Am. Chem. Soc*, 2002, 124, 14397-14402]. Subsequently, the reaction mixture was filtered to remove the resin and concentrated in vacuo. After the purification of glycosylated compound by silica-gel flash column chromatography (ethyl acetate:ethanol=10:1 to 5:1), the desired compound was a mixture of α and β anomers in 2:1 ratio (total yield 74%) confirmed by nuclear magnetic resonance (NMR). The free hydroxyl groups on the resulting (2-bromoethyl)-D-glucoside (2.7 g, 9.5 mmol) were benzoylated in pyridine (60 mL) by drop-wise addition of benzoyl chloride (8.8 mL, 76 mmol) over 10 min at 0° C., followed by stirring at room temperature for overnight in the presence of dimethylaminopyridine (DMAP) (116 mg, 0.952 mmol) [a) M. A. Maier, C. G. Yannopoulos, N. Mohamed, A. Roland, H. Fritz, V. Mohan, G. Just, M. Manoharan, *Bioconjugate Chem.* 2003, 14, 1829; b) R. E. Campbell, M. E. Tanner, *J. Org. Chem.* 1999, 64, 9487-9492]. The mixture was quenched with the addition of methanol (10 mL) and the reaction mixture was diluted with ethyl acetate. The organic layer was washed with the 1N hydrochloric acid (HCl) and sat. sodium bicarbonate (NaHCO$_3$), and dried over anhydrous magnesium sulfate (MgSO$_4$). Then, the organic layer was filtered and condensed under reduced pressure, each of the desired anomers was successfully isolated by silica-gel flash column chromatography (ethyl acetate:n-hexane=1:3) in a 2:1 (α:β) ratio, and the desired compound (2) was obtained.

$^1$H NMR (300 MHz, CDCl$_3$) δ8.097.89 (m, 8H), 7.547.31 (m, 12H), 6.23 (t, J=9.9 Hz, 1H), 5.70 (t, J=9.9 Hz, 1H), 5.44 (d, J=3.6 Hz, 1H), 5.33 (dd, J=10.1, 3.7 Hz, 1H), 4.644.56 (m, 2H), 4.48 (dd, J=11.9, 5.1 Hz, 1H), 4.164.03 (m, 1H), 3.943.85 (m, 1H), 3.763.70 (m, 2H);

$^{13}$C NMR (75 MHz, CDCl$_3$) δ166.20, 165.88, 165.78, 165.30, 133.48, 133.19, 129.98, 129.91, 129.76, 129.72, 129.63, 129.10, 128.93, 128.79, 128.45, 128.32, 96.31, 71.83, 70.30, 69.34, 68.92, 68.31, 62.95, 29.80; MALDI TOF MS calcd for C$_{36}$H$_{43}$O$_{12}$[M+H]$^+$: 703.11; found: 703.05.

2. Preparation of [2-(N-boc-piperazinoethyl)]-2,3,4,6-tetra-O-benzoyl-α-D-glucoside (3)

To a solution of the obtained compound (2) (230 mg, 0.327 mmol) in 1 mL anhydrous DMF was added N-Boc-piperazine (183 mg, 0.981 mmol) and TEA (182 µL, 1.308 mmol), and the reaction mixture was stirred at 80° C. After the reaction completion monitored by TLC, the resulting solution was diluted with distilled water, then extracted with ethyl acetate. The combined organic layer was washed with brine and condensed under reduced pressure. The desired compound (3) was purified by silica-gel flash column chromatography (n-hexane:ethylacetate=1:1→dichloromethane:methanol=10:1) as a yellowish oil (185 mg, 70%).

$^1$H NMR (500 MHz, CDCl$_3$) δ8.05-7.86 (m, 8H), 7.57-7.28 (m, 12H), 6.18 (t, J=10 Hz, 1H), 5.68 (t, J=9.5 Hz, 1H), 5.43 (d, J=3.5 Hz, 1H), 5.29 (dd, J=10.0, 3.5 Hz, 1H), 4.63-4.59 (m, 1H), 4.49-4.45 (m, 2H), 3.89 (ddd, J=11.0, 5.5, 5.0 Hz, 1H), 3.67 (ddd, J=11.0, 6.0, 5.0 Hz, 1H), 3.23 (bs, 4H), 2.65-2.58 (m, 2H), 2.35 (bs, 4H), 1.44 (s, 9H);

$^{13}$C NMR (125 MHz, CDCl$_3$) δ166.62, 166.30, 166.16, 165.78, 155.11, 133.99, 133.92, 133.64, 130.33, 130.20, 130.16, 130.13, 129.62, 129.44, 129.34, 128.97, 128.90, 128.78, 96.38, 96.32, 80.01, 72.42, 70.88, 70.00, 68.73, 66.73, 63.51, 57.92, 53.87, 28.91; LC MS calcd for C$_{45}$H$_{49}$N$_2$O$_{12}$[M+H]$^+$: 809; found: 809

3. Preparation of [2-(N-Cy3-piperazinoethyl)]-α-D-glucose (4)

For the deprotection of Boc group on the amine of compound (3) (45 mg, 0.056 mmol), 50% TFA in dichloromethane was added to the residue, followed by the concentration by N$_2$ purging. The resulting deprotected residue in DMF (300 µL) was basified with DIPEA and added to a solution of Cy3-COOH (17 mg, 0.037 mmol) and EDC (17 mg, 0.112 mmol) or PyAOP (58 mg, 0.112 mmol) in 100 µL DMF. The reaction mixture was stirred at room temperature and the reaction completion was monitored by HPLC analysis. After concentration under reduced pressure, the concentrate was dissolved in 1 mL of methanol to which sodium methoxide (0.5 M in Metanol, 290 µL, 0.145 mmol) was then added for debenzoylation. After the reaction was completed, the mixture was neutralized with methanolic HCl and subjected to HPLC to elute a fraction of the debenzoylated compound. The elution protocol for analytical HPLC is following: (1) 95% water and 5% acetonitrile for 1 min, (2) a linear gradient to 60% water and 40% acetonitrile over 4 min, (3) a linear gradient to 50% water and 50% acetonitrile over 10 min, (4) a linear gradient to 0% water and 100% acetonitrile over 5 min, (5) 0% water and 100% acetonitrile for 10 min, (6) 95% water and 5% acetonitrile for 10 min. Purification by prep-HPLC afforded the desired compound (4) (22 mg, 85%) (retention time: 12 min).

$^1$H NMR (500 MHz, CD$_3$OD) δ 8.55 (t, J=13.5 Hz, 1H), 7.54 (d, J=7.5 Hz, 2H), 7.47-7.30 (m, 6H), 6.45 (dd, J=13.4, 9.0 Hz, 2H), 4.20-4.17 (m, 2H), 4.08-4.05 (m, 1H), 3.83-3.80 (m, 3H), 3.67 (s, 3H) 3.63-3.42 (m, 12H), 2.57-2.54 (m, 2H), 1.97-1.79 (m, 6H), 1.78 (s, 6H), 1.77 (s, 6H);

$^{13}$C NMR (125 MHz, CD$_3$OD) δ 175.56, 174.86, 172.06, 151.01, 142.88, 142.20, 141.03, 140.90, 128.80, 125.64, 125.58, 122.35, 122.21, 111.28, 111.11, 102.60, 102.51, 99.20, 73.71, 73.32, 71.96, 70.35, 61.46, 60.82, 56.16, 55.35, 49.48, 49.45, 43.87, 38.37, 31.68, 30.57, 27.14, 26.98, 26.98, 26.90, 21.91; HRMS (FAB$^+$): calcd for C$_{41}$H$_{57}$N$_4$O$_7$ [M]$^+$: 717.4227; found: 717.4235.

EXAMPLE 3

Synthesis of [2-(N-Cy3-cyclohexane-1,4-diaminoethyl)]-α-D-glucose (GB5-Cy3)

a) 2-bromoethanol, Dowex 50WX8-400 ion exchange resin, 70° C. reflux; b) benzoyl chloride, pyridine, dimethylaminopyridine (DMAP); e) N-Boc-cyclohexane-1,4-diamine, triethylamine, dimethylformamide (DMF), 80° C.; d)(i) 50% trifluoroacetic acid (TFA), dichloromethane (DCM) (ii) Cy3-COOH, EDC, diisopropylethylamine (DIPEA), dimethylformamide (DMF) (iii) sodium methoxide (NaOMe), methanol 1. Preparation of (2-bromoethyl)-2,3,4,6-tetra-O-benzoyl-α-D-glucoside (2)

The same procedure of Example 2-1 was repeated to give the compound (2)

2. Preparation of [2-(N-boc-cyclohexane-1,4-diaminoethyl)]-2,3,4,6-tetra-O-benzoyl-α-D-glucoside (5)

To a solution of the obtained compound (2) (75 mg, 0.107 mmol) in 1 mL anhydrous DMF was added N-Boc-cyclohexane-1,4-diamine (69 mg, 0.322 mmol) and TEA (60 µL, 0.428 mmol), and the reaction mixture was stirred at 80° C. After the reaction completion monitored by TLC, the resulting solution was diluted with distilled water, then extracted with ethyl acetate. The combined organic layer was washed with brine and condensed under reduced pressure. The desired compound (5) was purified by silica-gel flash column chromatography (n-hexane:ethylacetate=1:1→dichloromethane:methanol=10:1) as a yellowish oil (45 mg, 50%)

$^1$H NMR (500 MHz, CDCl$_3$) δ8.10-7.87 (m, 8H), 7.57-7.28 (m, 12H), 6.19 (dd, J=10.0, 10.0 Hz, 1H), 5.69 (dd, J=10.0, 9.5 Hz, 1H), 5.38 (d, J=3.5 Hz, 1H), 5.30 (dd, J=10.0, 3.5 Hz, 1H), 4.61-4.59 (m, 1H), 4.99-4.43 (m, 2H), 3.95-3.93 (m, 1H), 3.62-3.59 (m, 1H), 2.87-2.78 (m, 2H), 2.33-2.31 (m,

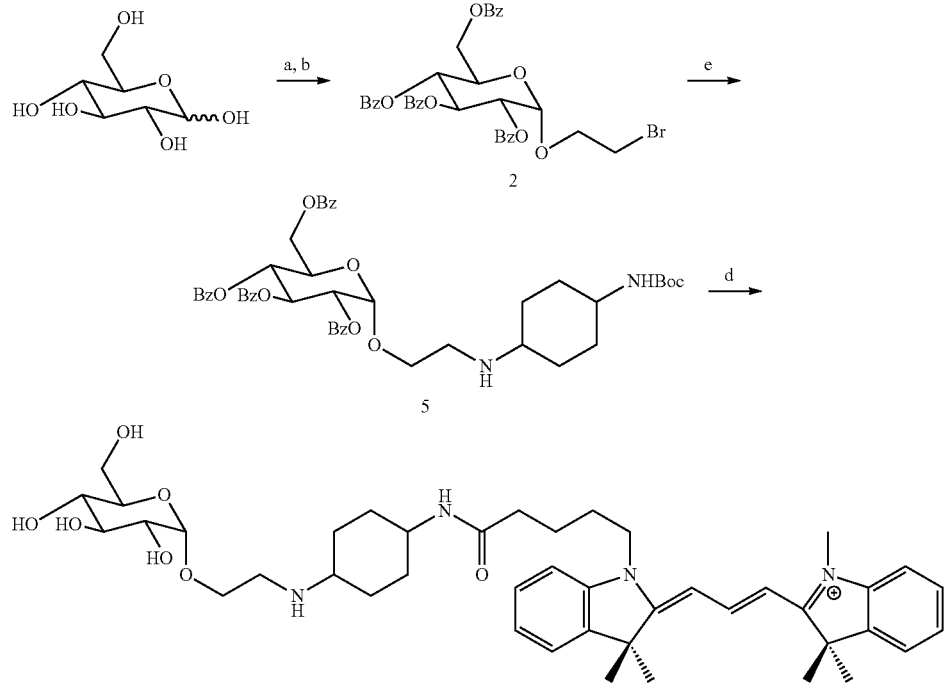

[Reaction Scheme 3]

1H), 2.03-2.02 (m, 2H), 1.96-1.87 (m, 2H), 1.73-1.68 (m, 2H), 1.44 (s, 9H), 1.30-1.21 (m, 3H), 1.05-0.96 (m, 3H); LC/MS calcd for $C_{47}H_{53}N_2O_{12}$ [M+H]$^+$: 837; found: 837.

3. Preparation of [2-(N-Cy3-cyclohexane-1,4-diaminoethyl)]-α-D-glucose (6)

The compound (6) was prepared in the same manner as in Example 2-3, with the exception that the compound (5) was used instead of the compound (3) (3 mg, yield: 16%).

$^1$H NMR (300 MHz, CD$_3$CD) δ 8.58 (t, J=13.4 Hz, 1H), 7.57 (d, J=7.3 Hz, 2H), 7.51-7.44 (m, 2H), 7.40-7.31 (m, 4H), 6.47 (dd, J=13.4, 2.0 Hz, 2H), 4.22-4.17 (m, 2H), 4.05-4.01 (m, 1H), 3.88-3.83 (m, 1H), 3.71 (s, 3H), 3.71-3.50 (m, 7H), 3.28-3.21 (m, 2H), 2.32-2.27 (m, 2H), 2.21-2.20 (m, 2H), 2.05-2.01 (m, 3H), 1.97-1.79 (m, 14H), 1.58-1.31 (m, 6H); HRMS (FAB$^+$): calcd for $C_{43}H_{61}N_4O_7$ [M]$^+$: 745.4540; found: 745.4545.

EXAMPLE 4

Synthesis of [2-(4-Cy3-aminobenzylaminoethyl)]-α-D-glucose (GB6-Cy3)

1. Preparation of (2-bromoethyl)-2,3,4,6-tetra-O-benzoyl-α-D-glucoside (2)

The same procedure as in Example 2-1 was repeated to give the compound (2).

2. Preparation of [2-(4-Boc-aminobenzylaminoethyl)]-2,3,4,6-tetra-O-benzoyl-α-D-glucoside (7)

To a solution of the obtained compound (2) (50 mg, 0.072 mmol) in 1 mL anhydrous DMF was added 4-Boc-aminobenzylamine (48 mg, 0.216 mmol) and TEA (40 μL, 0.288 mmol), and the reaction mixture was stirred at 80° C. After the reaction completion monitored by TLC, the resulting solution was diluted with distilled water, then extracted with ethyl acetate. The combined organic layer was washed with brine and condensed under reduced pressure. The desired compound (7) was purified by silica-gel flash column chromatography (n-hexane:ethylacetate=1:1→dichloromethane:methanol=10:1) as a yellowish oil (30 mg, 56%)

$^1$H NMR (500 MHz, CDCl$_3$) δ 8.05-7.86 (m, 8H), 7.56-7.28 (m, 12H), 7.03-7.01 (m, 2H), 6.59-6.57 (m, 2H), 6.19 (dd, J=10.0, 10.0 Hz, 1H), 5.69 (dd, J=10.5, 10.0 Hz, 1H), 5.39-5.32 (m, 2H), 4.58 (d, J=11.0 Hz, 1H), 4.48-4.43 (m, 2H), 3.97-3.95 (m, 1H), 3.65-3.63 (m, 3H), 2.92-2.82 (m, 2H);

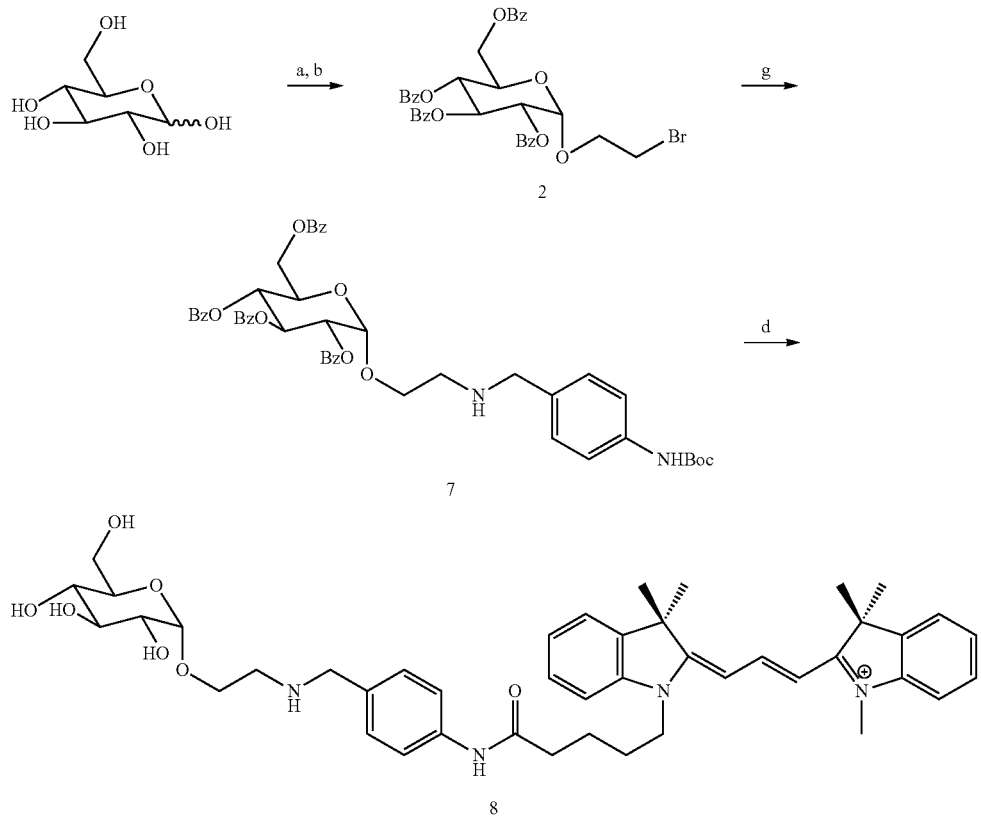

[Reaction Scheme 4]

a) 2-bromoethanol, Dowex 50WX8-400 ion exchange resin, 70° C. reflux; b) benzoyl chloride, pyridine, DMAP; g) 4-Boc-aminobenzylamine, triethylamine, DMF, 80° C.; d)(i) 50% TFA, DCM (ii) Cy3-COOH, EDC, DIPEA, DMF (iii) NaOMe, methanol $^{13}$C NMR (125 MHz, CDCl$_3$) δ 167.77, 166.42, 166.08, 165.96, 165.50, 133.91, 133.65, 133.36, 130.52, 130.26, 130.13, 130.08, 129.98, 129.94, 129.89, 129.63, 129.36, 129.13, 129.11, 128.72, 128.66, 115.38, 96.49, 72.12, 70.72, 69.68, 68.12, 63.14, 53.07, 47.76; LC/MS calcd for $C_{43}H_{40}N_2O_{10}$ [M+H]$^+$: 745; found: 745.

3. Preparation of [2-(4-Cy3-aminobenzylaminoethyl)]-α-D-glucose (8)

The compound (8) was prepared in the same manner as in Example 2-3 with the exception that the compound (7) was used instead of the compound (3) (6 mg, yield: 35%).

$^1$H NMR (300 MHz, CD$_3$OD) δ 8.58 (t, J=13.4 Hz, 1H), 7.53 (d, J=7.1 Hz, 2H), 7.47-7.28 (m, 10H), 6.48-6.43 (m, 2H), 4.80-4.67 (m, 3H), 4.20-4.17 (m, 2H), 3.96-3.92 (m, 1H), 3.83-3.76 (m, 2H), 3.71-3.67 (m, 4H), 3.65-3.54 (m, 5H), 3.48-3.43 (m, 3H), 2.73-2.70 (m, 1H), 1.93-1.77 (m, 2H), 1.77 (bs, 12H); HRMS (FAB+): calcd for C$_{44}$H$_{57}$N$_4$O$_7$ [M]+: 753.4227; found: 753.4209.

EXPERIMENTAL EXAMPLE

Purchase of Materials

D-(+)-glucose, acetic anhydride, sodium methoxide (0.5 M solution in methanol), fluorescein isothiocyanate, benzoyl chloride, piperazine, pyridine, dimethylformamide (DMF), dimethyl sulfoxide (DMSO), and the trifluoroacetic acid (TFA) were purchased from Sigma-Aldrich (St. Louis, Mo., USA). N,N-diisopropylethylamine, triethylamine, and 2-bromoethanol were purchased from TCI (Japan). The $^1$H and $^{13}$C NMR spectra were recorded on a Broker DRX-300 (Bruker Biospin, Germany) and Varian Inova-500 (Varian Assoc., Palo Alto, USA), and chemical shifts were measured in ppm downfield from internal tetramethylsilane (TMS) standard. The desired products were identified with MALDI-TOF MS and LC-MS analysis using Bruker Daltonics® (Germany). The identity of the final compounds was confirmed by high-resolution mass spectrometry (HRMS). HRMS analysis was performed at the Mass spectrometry facility of the National Center for Inter-university Research Facilities, Seoul National University. Density gradient reverse phase HPLC analysis was performed on a VP-ODS C-18 column (150×4.6 mm) at a flow rate of 1.0 mL/min for analysis, and PRC-ODS C-18 column (250×20 mm) at a flow rate of 10.0 mL/min for preparation, Shimadzu LC-6AD pump, SPD-10A detector (Japan). HPLC solvents consisted of deionized water containing 0.1% TFA (eluent A) and acetonitrile containing 0.1% TFA (eluent B).

High-glucose DMEM, low-glucose DMEM, glucose-depleted DMEM, RPMI1640, glucose-depleted RPMI1640, fetal bovine serum (FBS), horse serum, heat-inactivated bovine bovine serum, antibiotic-antimycotic solutions were purchased from GIBCO [Carlsbad, Calif., USA]. PBS and glucose solution were purchased from Welgene Inc. (Seoul, South Korea). Insulin and dexamethasone were purchased from SIGMA (USA). Rosiglitazone was purchased from Alexis (USA). AICAR (aminoimidazole carboxamide ribonucleotide) was purchased from Toronto Research Chemical (Canada). Microscope cover glasses were purchased from Marlenfeld GmbH & Co., KG (Germany). Images of fluorescence microscope were obtained with Olympus IX71 Fluorescence Microscope (Japan). Images of confocal laser scanning microscopy (CLSM) were obtained with a Carl Zeiss-LSM510 Microscope. FACS tabes were purchased from BD Biosciences (USA). Flow cytometric analysis was performed at FACSCalibur™ of BD Biosciences.

Cell Culture

A549 human lung melanoma cells, HeLa human cervical carcinoma cells, NIH/3T3 murine fibroblast cells, WI-38 human lung fibroblast cells, 3T3/L1 mouse fibroblast cells (preadipocyte) and C2C12 mouse myoblast cells were obtained from American Type Culture Collection (ATCC, Manassas, Va., USA).

NIH/3T3 cells were maintained in DMEM (United Search Partners, Austin, Tex., USA) supplemented with heat-inactivated 10% (v/v) fetal bovine serum (FBS, United Search Partners, Austin, Tex., USA) and 1% (v/v) antibiotic-antimycotic solution. A549 cells, HeLa cells and WI-38 cells were maintained in RPMI 1640 (United Search Partners, Austin, Tex., USA) supplemented with heat-inactivated 10% (v/v) fetal bovine serum and 1% (v/v) antibiotic-antimycotic solution. 3T3/L1 mouse fibroblast cells were maintained in DMEM supplemented with 10% heat-inactivated bovine serum and 1% antibiotic-antimycotic solution. C2C12 cells were maintained in DMEM supplemented with 10% FBS and 1% antibiotic-antimycotic solution.

All cell lines were maintained in a humidified atmosphere of 5% CO$_2$ and 95% air at 37° C., and cultured in T75 Flask (Nalge Nunc International, Naperville, Ind., USA) in order to observe fluorescence emission by confocal laser scanning microscopy (CLSM). All cell lines were maintained between $5\times10^5$ and $1\times10^6$ cells/mL according to the ATCC culture guide lines.

Differentiation of Cell Lines

For the differentiation of preadipocyte to mature adipocytes, 3T3/L1 fibroblast cells were cultured using the above mentioned culture protocol. When 3T3/L1 fibroblast cells reached to 100% confluency, the differentiation toward mature adipocytes was induced by changing media with DMEM containing 10% FBS, 5 μg/mL insulin, 10 μM rosiglitazone, and 1 μM dexamethasone. After the 2-day incubation, the culture medium was changed to DMEM containing only FBS and insulin in every two days. When the cells start to generate lipid drops as an indication of the differentiation toward mature adipocytes, insulin was removed from the culture media. Mature adipocytes can be achieved by 8- to 12-day differentiation, and used for flow cytometric analysis and fluorescent bioimaging microscopy.

For the differentiation to mature muscle cells, C2C12 mouse myoblast cells were maintained in DMEM supplemented with 10% FBS and 1% antibiotic-antimycotic solution. When the cells reached to 100% confluency, the medium was changed to DMEM containing 2% horse serum in every two days. Experiments for flow cytometric analysis and flow cytometric analysis were carried out with cells after 3 to 5-days differentiation.

Protocol of Confocal Laser Scanning Microscope (CLSM)

$1\times10^4$ cells were cultured on a Lab-Tek glass chamber slide (Nalge Nunc International, Naperville, Ind., USA) in 35 mm cell culture dish. After 24 h, the glass chamber slide was taken from culture dish and loaded on chamber. Then, the chamber was attached to the microscope. The temperature of the chamber was maintained at 37° C. After injection of 12.5 μM of Cy3-Glc-α in RPMI 1640 in the chamber, the fluorescent image was taken every 60 sec, digitized, and saved on a computer for later analysis.

Also, C2C12 cells and 3T3/L1 cells, each having a population of $6\times10^4$ cells, were cultured and differentiated on respective microscope cover glasses [Marlenfeld GmbH&Co., KG (Germany)] in 35 mm cell culture dishes. After removal of the differentiation media, FBS-free DMEM media containing 5.5 mM glucose were added to maintained a serum-free condition for 4 hrs. Then, insulin (100 nM) or AICAR (1 mM) was added. In this regard, an FBS-free DMEM medium containing 5.5 mM glucose or a DMEM medium free of both FBS and glucose was used. Cells were incubated at 37° C. for 30 min after which the glass chamber slides were withdrawn from the culture dishes and loaded on a chamber. While being maintained at 37° C., the chamber was mounted on a microscope. The medium within the chamber was replaced with a glucose-depleted medium (DMEM, glucose free, GIBCO) containing Cy3. Fluorescence images were taken every seven seconds, digitized and saved on a computer until analysis.

Protocol of Inverted Fluorescent Microscope $1 \times 10^4$ cells were cultured on a Lab-Tek glass chamber slide (Nalge Nunc International, Naperville, Ind., USA) in 35 mm cell culture dish. After 24 h, the cells were treated for each experimental purpose. Then, the medium was replaced with RPMI 1640 medium containing 12.5 μM of Cy3-Glc-α. The cells were exposed to Cy3-Glc-α for 40 min, then washed with PBS 3 times. Finally, the glass chamber slide was taken from culture dish and loaded on the fluorescence microscope (Axiovert 200, Carl Zeiss, Germany). Fluorescence images of 35-50 cells were taken by CCD camera (Axiocam MRm, Germany) and fluorescence intensity of each cell was measured by Axiovision (program for data analysis). An area as ROIs (regions of interest) which contains a cell in phase-contrast image was drawn using Axiovision. Axiovision analyzed CCD camera images and provided the digitized mean of fluorescence intensity in the ROIs that the present inventors had established. The present inventors subtracted the background intensity from the fluorescence intensity to get the fluorescence intensity value that a cell contained. With the method described above, the present inventors digitized fluorescence intensity and performed various experiments.

Also, NIH/3T3, A549, C2C12 and 3T3/L1 cells, each having a population of $4 \times 10^4$ cells, were cultured on 35 mm cell culture dishes (BD Falcon™ Cell Culture Dish; BD Bioscience, CA, USA). Two days later, the cell culture medium was replaced with a glucose-depleted medium (DMEM, glucose free, GIBCO) supplemented with 0 mM, 11 mM or 55 mM D-glucose and 10 μM GB2-Cy3. After incubation at 37° C. for 30 min, the cells on the cover slips in the 35-mm cell culture dishes were washed twice with cold PBS and the cover slips were mounted on the caster of a fluorescence microscope (Olympus IX71). During observation under the fluorescence microscope, the cells were maintained at 37° C. in the chamber. Fluorescence images of 35-50 cells were taken by CCD camera (Axiocam MRm, Germany) and each cell was measured for fluorescence intensity using the image data analysis program Image-Pro® Plus (MediaCybernetics, USA). As ROIs (regions of interest), areas which encompassed cells within phase-contrast images were drawn using Image-Pro® Plus. Image-Pro® Plus analyzed CCD camera images to produce the digitized mean of fluorescence intensity within the ROIs that the present inventors had established. The background intensity was subtracted from the detected fluorescence intensity to give the fluorescence intensity value that a cell contained. In this manner, the fluorescence intensity was digitized for performing various experiments.

Experimental Example 1

(1) To evaluate the applicability of the fluorescent glucose analogue (Cy3-Glc-α) of the present invention, finally obtained in Example 1, as a bioprobe, the intracellular uptake efficiency of Cy3-Glc-α was measured by using a confocal laser scanning microscope (CLSM). That is, in order to decide the optimum concentration of the analogue, A549 cells (non-small cell lung cancer cell in human lung carcinoma) were allowed to incorporate the analogue at a concentration of 6 μM, 12.5 μM, 25 μM, 50 μM, and 100 μM.

Figure 13:
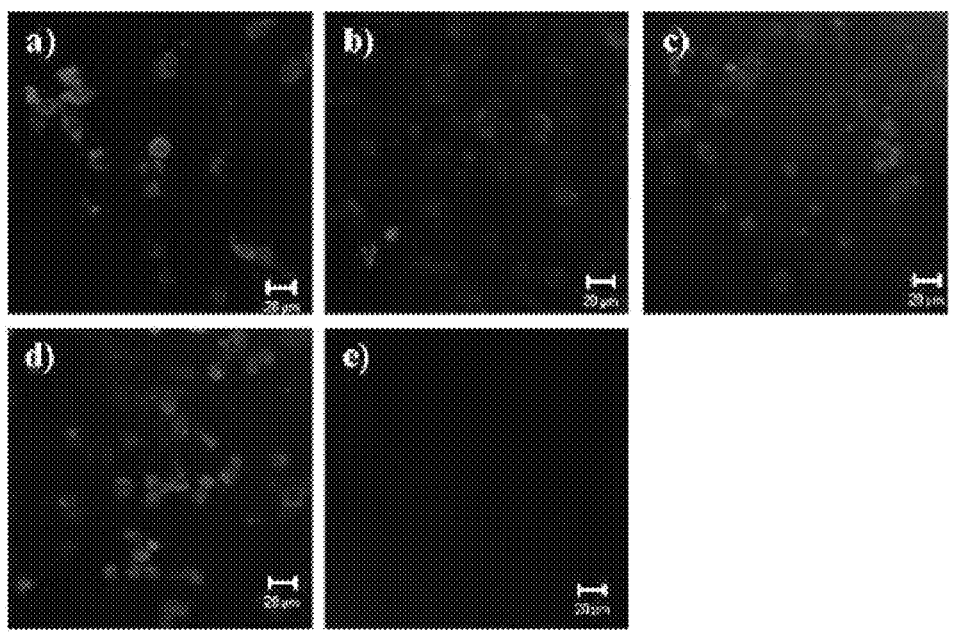
FIG. 13 illustrates pictures of uptake efficiency in A549 cells according to the concentration of an α glucose anomer (Cy3-Glc-α) which was taken by using a confocal laser scanning microscope (CLSM) [a) 100 µM, b) 50 µM, c) 25 µM, d) 12.5 µM, and e) 6 µM].

The results are shown in FIG. 13. As shown in FIG. 13, based on the repeated tests, 12.5 μM was selected as the optimum concentration in cellular uptake experiments.

Figure 14:
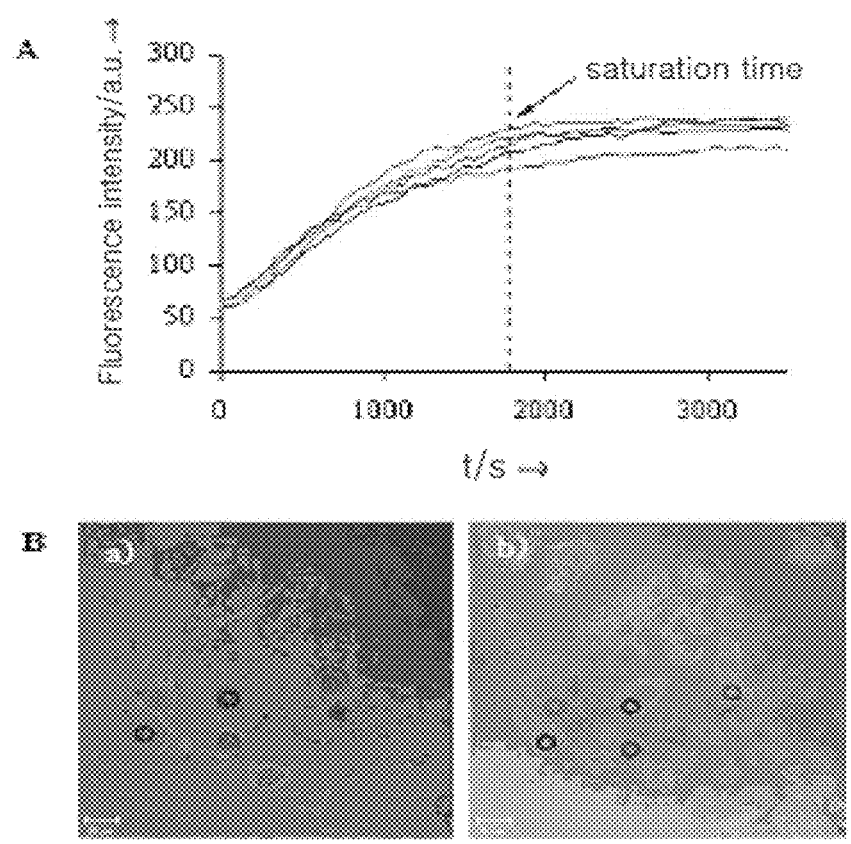
FIG. 14 illustrates the measurements of the uptake efficiency in A549 cells according to the incubation time of an α glucose anomer (Cy3-Glc-α).

(2) In addition, the experiment was performed by using the confocal laser scanning microscope to measure the optimum incubation time required to achieve the maximum uptake of the analogue Cy3-Glc-α. The results are shown in FIG. 14. As shown in FIG. 14, the uptake of Cy3-Glc-α by A549 cells reached the maximum within 35 min.

Under these optimized conditions, the experiment was performed to confirm whether or not the probe according to the present invention acts as a glucose analogue.

Experimental Example 2

(1) Compared to 2-NBDG, the bioprobe according to the present invention is an O-1-glycosylated glucose analogue at the C-1 position; therefore, both anomers were asymmetrically synthesized simultaneously under the assumption that the behavior of these anomers would be different, because the molecular conformations of Cy3-Glc-α and β glucose anomer (hereinafter, referred to as "Cy3-Glc-β") are quite distinct from each other.

Figure 15:
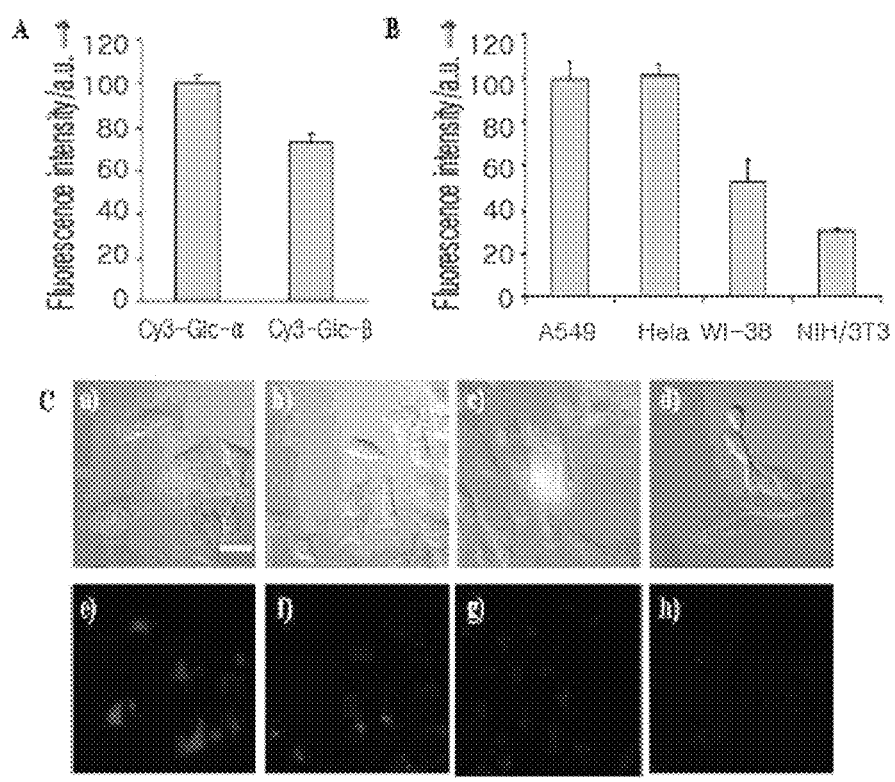
FIG. 15A is a graph that illustrates the Cy3-Glc-α and Cy3-Glc-β uptake by A549 cells. The fluorescence intensities are expressed as an arbitrary unit (a.u.) determined by fluorometry, and data are the mean of 30-50 cells from an experimental representative of at least two independent experiments.
FIG. 15B is a graph that illustrates the efficiency of Cy3-Glc-α uptake in cancer cells (A549, HeLa) and normal cells (WI-38, NIH/3T3).
FIG. 15C illustrates pictures showing the Cy3-Glc-α uptake by A549 cells (a, e), HeLa cells (b, f), WI-38 cells (c, g) and NIH/3T3 cells (d, h). In connection with this, (a-d) are phase-contrast images, and (e-h) are fluorescence images (Scale bar in (a)=40 µm).

To confirm the above hypothesis, real-time uptake of Cy3-Glc-α was measured, and the results were compared to those of Cy3-Glc-β by live imaging of A549 cells by using inverted fluorescent microscope. As shown in FIG. 15A, the uptake of Cy3-Glc-α was 40% superior to that of Cy3-Glc-β. This led the present inventors to the conclusion that the stereochemistry at the C-1 anomeric position definitely influences the efficiency of mimicking glucose, and this might be due to the binding orientation of D-glucose in GLUTs [P. W. Hruz, M. M. Mueckler, *Mole. Memb. Biol.* 2001, 18, 183-193].

(2) Based on this observation, further studies in bioimaging and bioapplication were performed only with the α anomer as choice of the bioprobe. That is, the efficiency of Cy3-Glc-α uptake was measured, in particular, the differentiation of GLUT-overexpressing cancer cells (A549; lung carcinoma cell line, HeLa; cervical carcinoma cell line) was preponderantly tested instead of normal cells (WI-38; lung normal cell line, NIH/3T3; murine fibroblast cell line).

As shown in FIG. 15B, Cy3-Glc-α uptake in NIH/3T3 was only 30% that of A549 cells. Accordingly, the selective uptake of Cy3-Glc-α in cancer cells with enhanced glucose-metabolism was confirmed. This data demonstrated that the cellular uptake of Cy3-Glc-α depends on the higher glucose metabolism in cancer cells, which in turn relies on the ATP generated from glycolysis in order to meet the energy requirements of rapidly replicating tissue. Therefore, glucose metabolism is strongly correlated with the GLUT/hexokinase expression levels. From the data, it could be seen that Cy3-Glc-α according to the present invention was capable of being applied to molecular bioimaging and bioassay in cancer studies.

Meanwhile, FIG. 15C is a picture that illustrates the uptake of Cy3-Glc-α by A549 cells (a, e), HeLa cells (b, f), WI-38 cells (c, g) and NIH/3T3 cells (d, h).

Experimental Example 3

To confirm whether the intracellular uptake pathway of glucose analogues is relevant to that of D-glucose, the direct competition experiment has been utilized in many studies [M. Zhang, Z. Zhang, D. Blessington, H. Li, T. M. Busch, V. Madrak, J. Miles, B. Chance, J. D. Glickson, G. Zheng, *Bioconjugate Chem.* 2003, 14, 70-97; K. Yamada, M. Nakata, N. Horimoto, M. Saito, H. Matsuoka, N. Inagaki, *J. Biol. Chem.*

2000, 275, 22278-22283]. If the cellular uptake of a certain glucose analogue depends on the concentration of D-glucose but not on that of L-glucose, then that particular glucose analogue would enter the cell via a GLUT-mediated glucose uptake system.

Therefore, based on prior experiments, the process of the cellular uptake of Cy3-Glc-α was tested. The test was performed by measuring the efficiency of Cy3-Glc-α uptake by A549 cells in RPMI 1640 lacking glucose or containing 10 mM D-glucose, 50 mM D-glucose, and 50 mM L-glucose (37° C.).

Figure 16:
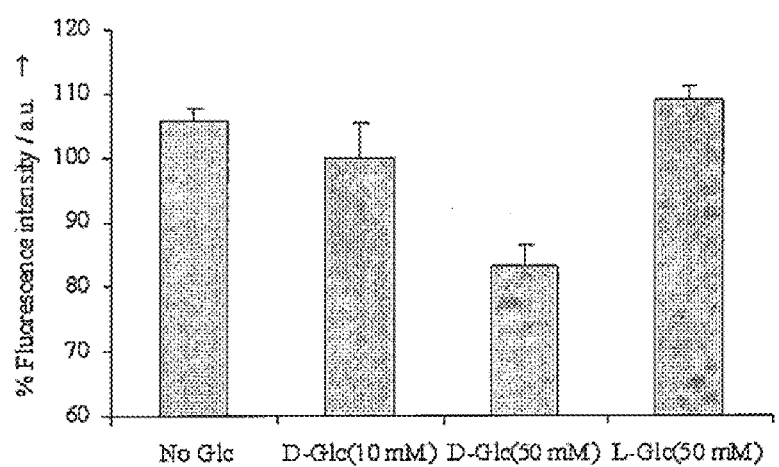
FIG. 16 is a graph that illustrates dose-dependent Cy3-Glc-α uptake inhibition in A549 cells when there is no D-glucose, 10 mM D-glucose or 50 mM D-glucose. To demonstrate specific inhibition by D-glucose, an identical experiment was performed in the presence of 50 mM L-glucose, which does not result in uptake inhibition. The fluorescence intensities are expressed as arbitrary units (a.u.) determined by the fluorometry, and the data are the mean of 35-50 cells from an experimental representative of at least two independent experiments.

As shown in FIG. 16, the uptake of Cy3-Glc-α decreased as the concentration of D-glucose in the medium increased. However, the uptake of Cy3-Glc-α was not influenced by the concentration of L-glucose in the medium. This suggests that Cy3-Glc-α is taken up by the cell through a glucose-specific transport system, not by passive diffusion. Therefore, Cy3-Glc-α can function as a D-glucose analogue and can be applied as a research tool in the study of glucose metabolism.

Experimental Example 4

Figure 17:
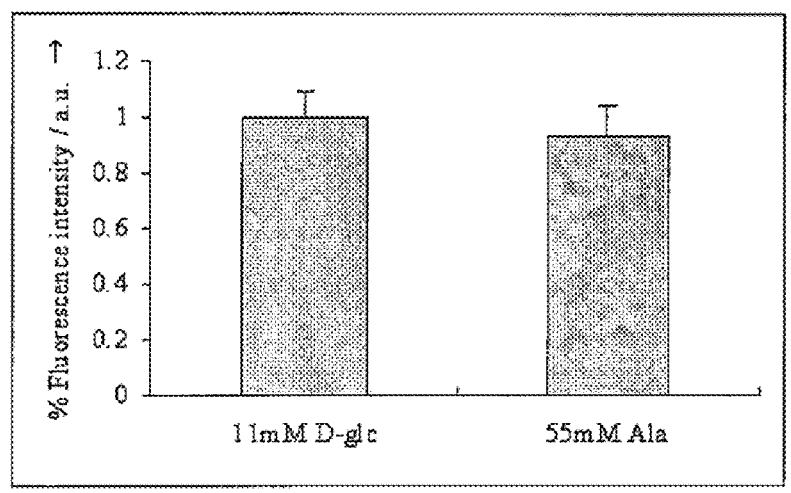
FIG. 17 is a graph that illustrates the uptake of Cy3-Glc-α using A549 cells in the absence or presence of 55 mM alanine.

In addition, the uptake of Cy3-Glc-α was measured using A549 cells in media containing 55 mM alanine in order to ensure that the osmotic pressure in the medium does not affect the uptake of Cy3-Glc-α. As shown in FIG. 17, there was no difference in the uptake efficiency under the media with or without 55 mM alanine. This demonstrates the fact that the osmotic pressure does not affect the uptake of Cy3-Glc-α by A549.

Experimental Example 5

It was confirmed that Cy3-Glc-α acted as a D-glucose analogue, and Cy3-Glc-α was compared to a fluorescent analogue of 2-deoxyglucose, for example, 2-NBDG [M. Zhang, Z. Zhang, D. Blessington, H. Li, T. M. Busch, V. Madrak, J. Miles, B. Chance, J. D. Glickson, G. Zheng, *Bioconjugate Chem.* 2003, 14, 7097; K. Yoshioka, H. Takahashi, T. Homma, M. Saito, K. B. Oh, Y. Nemoto, H. Matsuoka, *Biochim. Biophys. Acta.* 1996, 1289, 5-9; K. Yoshioka, M. Saito, K. B. Oh, Y. Nemoto, H. Matsuoka, M. Natsume, H. Abe, *Biosci. Biotech. Biochem.* 1996, 60, 1899-1901].

The cellular uptake of 2-NBDG was not detected under identical experimental conditions used for Cy3-Glc-α. Even when 125 μM of 2-NBDG was exposed to the lens of a CCD camera for 500 ms, the fluorescence was not detected. To achieve the fluorescence intensity with 2-NBDG to 80% that of Cy3-Glc-α, a 10 fold increase in 2-NBDG concentration and a 20 fold increase in the lens exposure time in D-glucose-depleted medium were needed.

Figure 18:
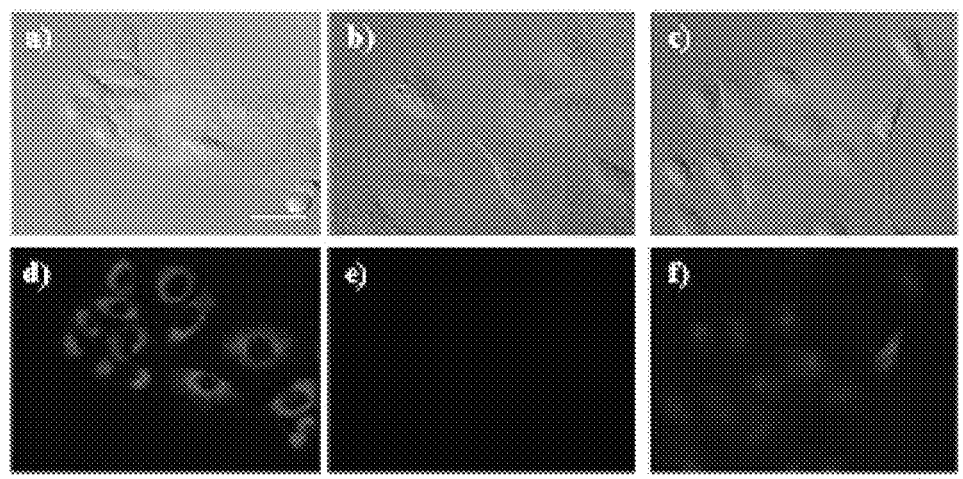
FIG. 18 illustrates the uptake image of 2-NBDG and Cy3-Glc-α by the A549 cells with different conditions. (a, d) are pictures that illustrate 12.5 µM of Cy3-Glc-α with a 500 ms lens exposure of the CCD camera. (b, e) are pictures that illustrate 12.5 µM of 2-NBDG with a 500 ms lens exposure of the CCD camera. (c, f) are pictures that illustrate 125 µM of 2-NBDG with a 11000 ms lens exposure of CCD camera. (a, b, c) illustrate the phase-contrast images in the A549 cells. (d, e, f) illustrate the fluorescence images in the A549 cells (Scale bar in (a)=40 µm).

In addition, the cellular uptake of 2-NBDG in normal media (containing 10 mM D-glucose) was extremely low (>60% uptake reduction in normal media) and was hardly detected using fluorescent based imaging methods [R. G. O'Neil, L. Wu, N. Mullani, *Mol. Imaging Biol.* 2005, 7, 388-392]. 2-NBDG was detectable only in glucose-depleted media, and this means a critical limitation of bioapplication of 2-NBDG in the biologically significant environments. In comparison with 2-NBDG, the reduction of Cy3-Glc-α uptake in glucose-containing media was only 5% compared to that in glucose-depleted media (FIG. 18). Therefore, it was confirmed that Cy3-Glc-α was capable of being applied to a bioassay system regardless of glucose starvation.

Experimental Example 6

(1) Based on the fact that Cy3-Glc-α could be taken up by cells as a D-glucose analogue through a D-glucose specific transport mechanism in normal glucose-containing medium, Cy3-Glc-α was applied to the screening of small molecular modulators involved in cellular metabolism. The application was performed under the postulation that the depression of perturbed cellular metabolism in cancer cells was caused by anticancer agents, which was closely related to the reduction of glucose uptake.

The present inventors intended to monitor this phenomenon by the fluorescent bioprobe according to the present invention, that is, Cy3-Glc-α. As a proof-of-principle experiment, after A549 cancer cells were treated with taxol (9.8 μM), an anticancer agent, and the uptake of Cy3-Glc-α was measured at 3, 6, 12, and 24 h after the treatment.

Figure 19:
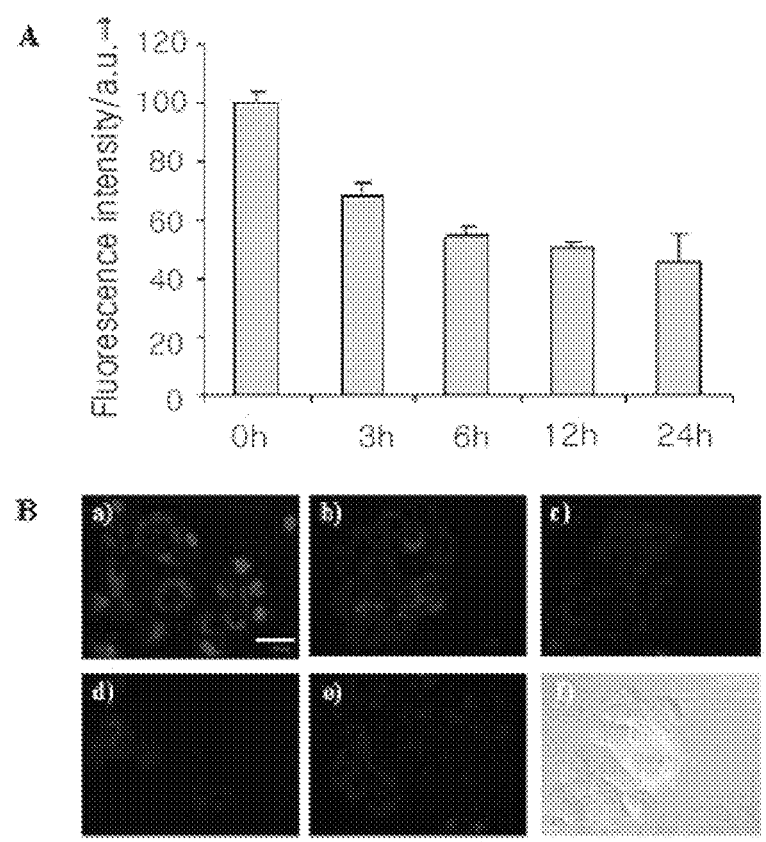
FIG. 19A is a graph that illustrates the Cy3-Glc-α uptake by A549 cells measured after 0, 3, 6, 12, and 24 h of treatment with taxol (9.8 µM) at 37° C. In connection with this, the fluorescence intensities are expressed as an arbitrary unit (a.u.) determined by fluorometry and the data are the mean of 35-50 cells from an experimental representative of at least two independent experiments.
FIG. 19B illustrates images showing the Cy3-Glc-α uptake by A549 cells after treatment with taxol (9.8 µM) at 37° C. for the following durations (a; 0 h, b; 3 h, c; 6 h, d; 12 h, e; 24 h, and f; phase-contrast image after 6 h incubation. After incubation with taxol, each image was captured with a fluorescent microscope after 30 min of Cy3-Glc-α treatment (Scale bar in (a)=40 µm).

As shown in FIG. 19, the cellular uptake of the probe reduced as the incubation time increased. This clearly demonstrates the potential of Cy3-Glc-α for evaluation of the metabolic perturbation caused by bioactive small molecules in live cells under physiological conditions.

Figure 20:
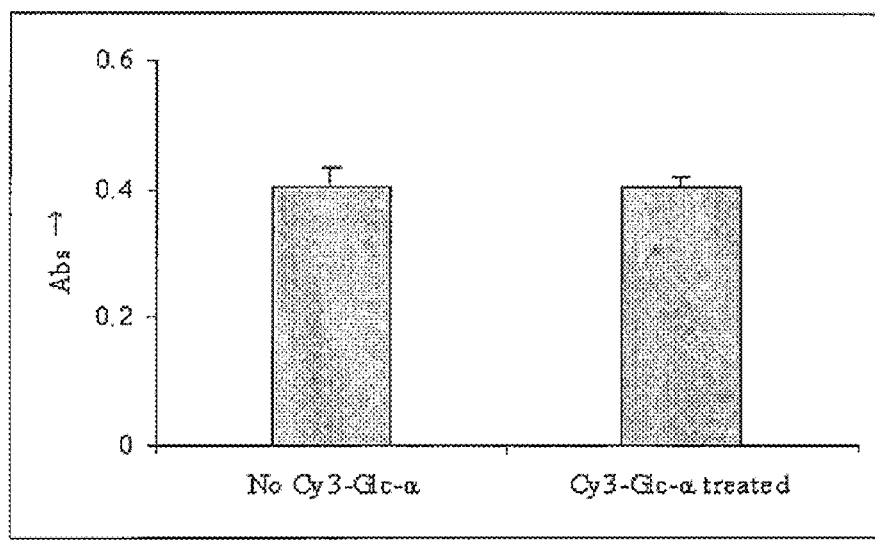
FIG. 20 is a graph that illustrates the measurement of the viability of cells treated with Cy3-Glc-α (12.5 µM) by using a CCK-8 kit.

(2) Therefore, Cy3-Glc-α should not affect cell viability. The viability of cells treated with Cy3-Glc-α (12.5 μM) by using a CCK-8 kit (Cell Counting Kit-8, Dojindo, Japan) was measured by using an ELISA plate reader (ELx800™, Bio-Tex, USA) DP. CCK-8 is a colorimetric assay for determining the number of viable cells in cell proliferation and cytotoxicity assays. The principle of measuring cell viability of CCK-8 is the same as that of MTT. However, CCK-8 is more sensitive than MTT. Hence the present inventors selected CCK-8 for the cell viability test. With the results given by CCK-8, as shown in FIG. 20, the present inventors could conclude that Cy3-Glc-α treatment does not affect cell viability in the present incubation condition.

(3) In addition, after the taxol concentration was changed in the range of 490 nM to 49 nM, the uptake of Cy3-Glc-α by A549 cells was measured after 8 hr and 12 hr, and after another anticancer agent, i.e., combretastatin, (2 μM) was used to treat A549 cells, the uptake of Cy3-Glc-α by A549 cells was measured after 8 hr and 12 hr.

From the following Table 1, it can be seen that the uptake of Cy3-Glc-α by A549 cells depended on the dose. In addition, combretastatin inhibited the multiplication of cells by obstructing cell metabolism, which could be seen by the reduction in the cellular uptake of Cy3-Glc-α.

TABLE 1

|  | 6 h | 12 h |
| --- | --- | --- |
| Taxol (9.8 μM) | 54.8% | 50.2% |
| Taxol (490 nM) | 88.4% | 61.8% |
| Taxol (49 nM) | 96.5% | 86.9% |
| Combretastatin (2 μM) | 57.4% | 45.0% |

Based on the above experiments, it is deemed that Cy3-Glc-α can be used to evaluate the behavior of bioactive small molecules in cells in a manner similar to the MTT assay [T. Mosmann, *J. Immunol. Methods.* 1983, 65, 55-63], which measures mitochondrial function. The advantages of a screening system with Cy3-Glc-α over an MTT assay are as follows. First, the measurement time is short. MTT assays usually take 24 hours and up to 72 hours in many cases, e.g. when taxol and combretastatin are used; whereas the screening system with Cy3-Glc-α showed significant difference in that it takes 6 hours to 12 hours. Second, the observation channel of a screening system with Cy3-Glc-α is quite different from that of a cell-viability assay, that is, the former involves measuring glucose-uptake efficiency, and the latter involves measuring mitochondria function. Therefore, it is deemed that the two assay systems will compensate for limitations of each other.

Experimental Example 7

Other fluorescent glucose analogues than Cy3-Glc-α were examined for acting efficiently as bioprobes for analyzing the cellular uptake of glucose. In this regard, the fluorescent glucose analogues were examined for competition with glucose for cellular uptake when typical glucose uptake routes were used, and analyzed for uptake efficiency.

1-1. Flow Cytometry

FACS (Fluorescence Activated Cell Sorting)-based flow cytometric analysis was used to compare cellular uptake efficiency in NIH/3T3 cells among the glucose probe [2-(N-Cy3-piperazinoethyl)]-α-D-glucose (GB2-Cy3), synthesized in Example 2, the conventional fluorescent glucose probe 2-NBDG and the glucose probe Cy3-Glc-α, synthesized in Example 1.

NIH/3T3 cells were cultured on 10 cm cell culture dishes and transferred in a volume of $3 \times 10^5$ cells into each FACS tube (5 mL, BD). They were washed once with cold PBS before incubation at 37° C. for 30 min in 11 mM D-glucose-containing PBS or glucose-free PBS in the presence of the bioprobe [GB2-Cy3 (5 μM), 2-NBDG (5 μM or 50 μM) or Cy3-Glc-α (5 μM)]. Cells that were incubated without the bioprobes were used as a negative control. After being washed with cold PBS, $1 \times 10^4$ NIH/3T3 cells were analyzed on FACSCalibur™ (FACS-based flow cytometer). GBs-Cy3 was detected by FL2 channels. Raw data of $1 \times 10^4$ cells are shown in histograms, with the mean values thereof given in the graph of FIG. 21.

Figure 21:
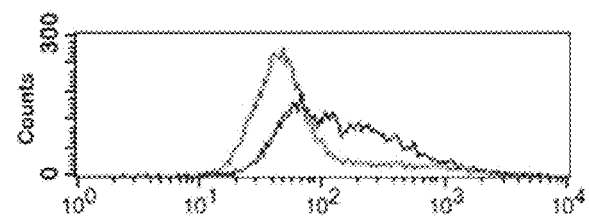
FIG. 21 is of FACS diagram plots showing the fluorescent intensities of NIH/3T3 cells treated respectively with GB2-Cy3 (5 µM), Cy3-Glc-α (5 µM), and 2-NBDG (5 µM and 50 µM) in the presence or absence of D-glucose a), a histogram showing fluorescent intensity of cells treated with GB2-Cy3, Cy3-Glc-α and 2-NBDG b), and a graph showing fluorescent intensities, with the normalization of D-glucose-depleted cells to c). (Black line: in the absence of glucose/red line: in the presence of 11 mM D-glucose)
Figure 21:
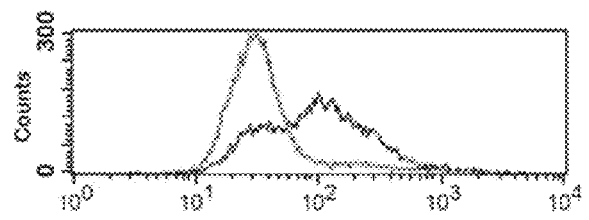
Figure 21:
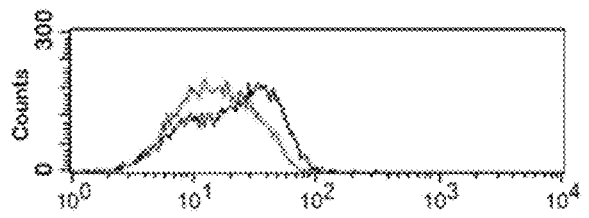
Figure 21:
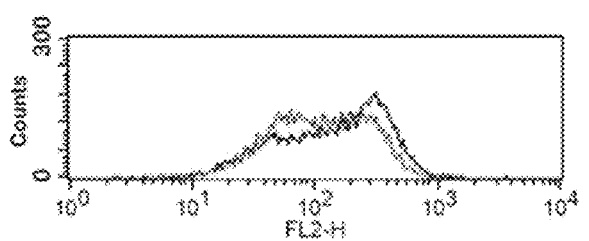
Figure 21:
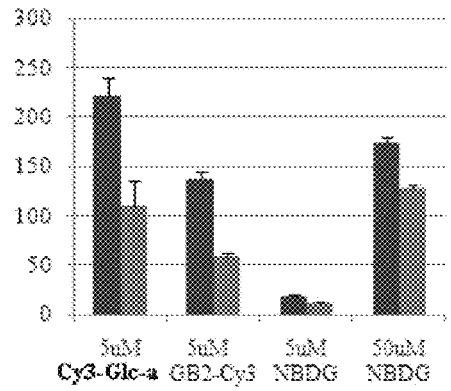
Figure 21:
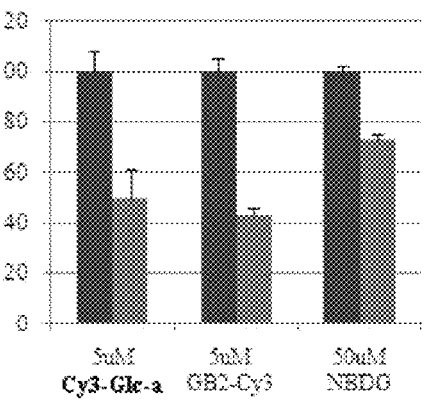

As shown in FIG. 21, NIH/3T3 cells were treated independently with 5 μM of the three glucose probes (Cy3-Glc-α, GB2-Cy3, and 2-NBDG) in the presence or absence of 11 mM D-glucose. The numerical values obtained from the flow cytometric histogram plots showed that 2-NBDG did not compete with D-glucose for cellular uptake, and that the fluorescent intensity of 2-NBDG remained constant at the basal level. The fluorescent intensity of 2-NBDG can be made comparable to that of GBs-Cy3 according to the present invention by using a concentration of 2-NBDG (50 μM) that is 10 times higher than that of GBs-Cy3 (5 μM). The average fluorescence intensity corresponding to the cellular uptake of Cy3-Glc-α, GB2-Cy3 (5 μM) and 2-NBDG (50 μM) under glucose-depleted condition was obtained from the histogram and normalized to 100; the reduction in the cellular uptake of 2-NBDG due to the competitive effect of 11 mM D-glucose was noted to be only 30%. However, the cellular uptake of GB2-Cy3 demonstrated a drastic reduction of about 60% and it is higher than the reduction in the cellular uptake of Cy3-Glc-α, about 50%. (See FIG. 21(c)). Therefore, the sensitivity of the probes Cy3-Glc-α and GB2-Cy3 according to the present invention is 10-times higher than that of the typical probe 2-NBDG.

Even when used at a concentration lower than that of 2-NBDG, as explained above, the inventive glucose probe GB2-Cy3 was observed to significantly decrease in cellular uptake by competition with D-glucose and to show high fluorescence intensity. Therefore, GB2-Cy3 is a probe which is very effective for monitoring the cellular uptake of glucose through a glucose uptake system.

1-2. Fluorescence Imaging Analysis

NIH/3T3 and A549 cells were cultured on microscope cover glasses in 35 mm cell culture dishes and subjected to fluorescence imaging analysis according to the protocol. The fluorescence images of the cells were taken and are given in FIG. 22.

Figure 22:
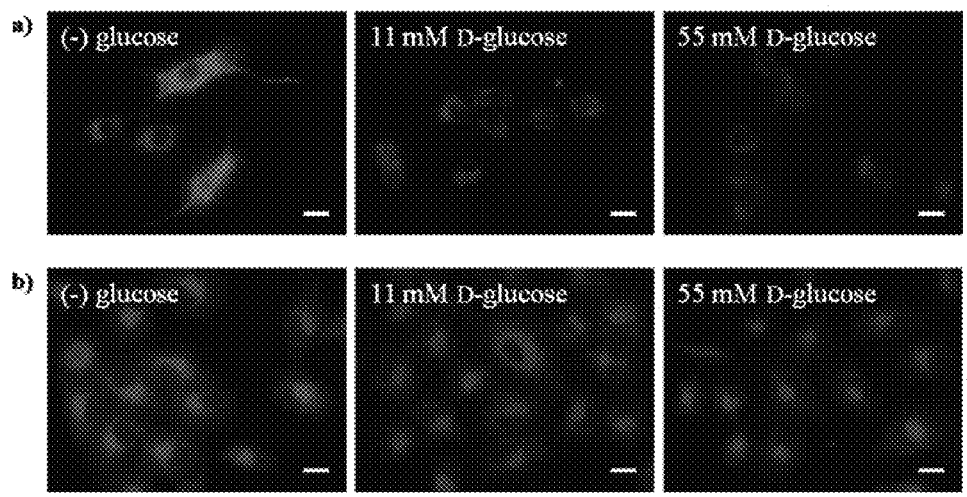
FIG. 22 is of fluorescence images showing competitive uptake of GB2-Cy3 (10 µM) in NIH/3T3 cells (a) and A549 cells (b) at various concentrations of D-glucose (scale bar=20 µm).
Figure 22:
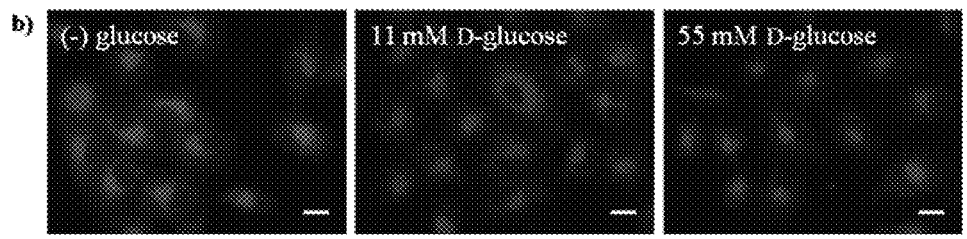

As seen in FIG. 22, the cellular uptake of GB2-Cy3 was reduced in a D-glucose dose-dependent manner. Also, the cellular uptake of GB2-Cy3 was observed to increase in A549 lung carcinoma cells, which have more active glucose metabolism (see FIG. 22B), indicating that the cellular uptake of GB2-Cy3 takes a passage for D-glucose in competition with D-glucose. Therefore, the fluorescent glucose analogue of the present invention is a very effective probe for monitoring the intracellular uptake of glucose in a glucose-uptake system.

Figure 24:
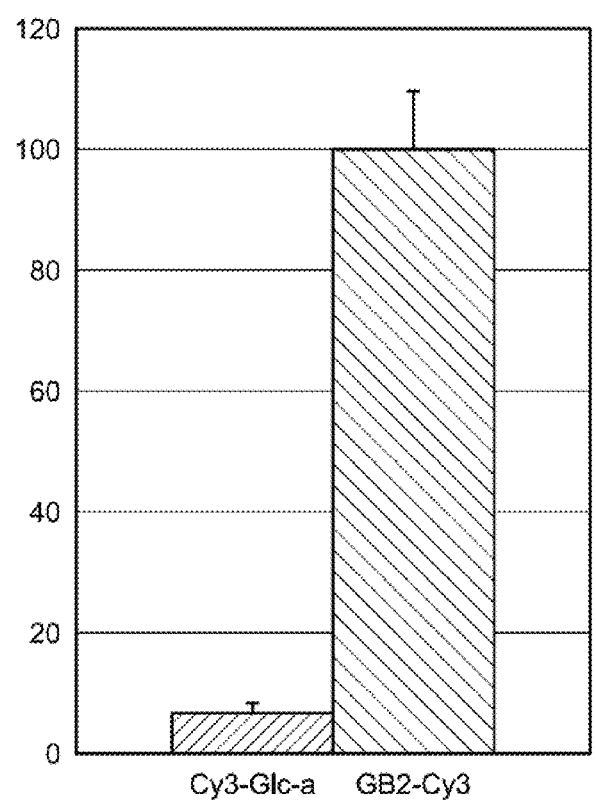
FIG. 24 is a histogram showing the comparison of fluorescent intensity between fluorescent glucose analogues introduced into cells in FIG. 23.
Figure 25:
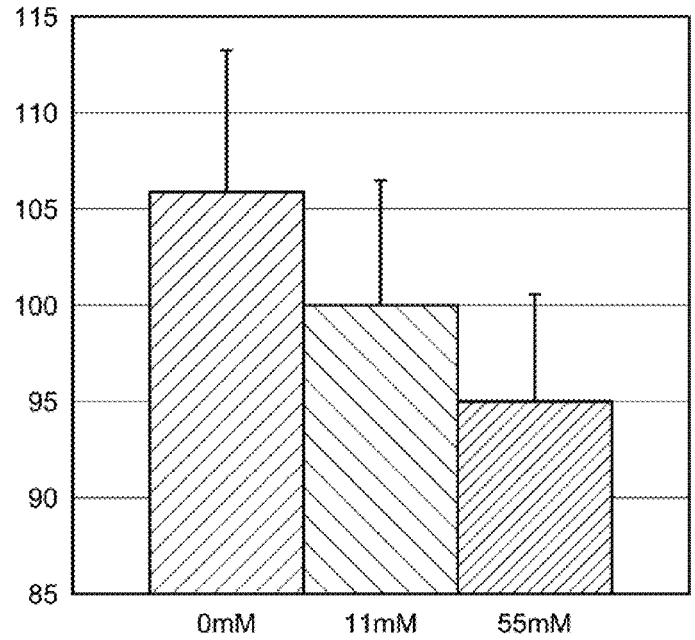
FIG. 25 is of graphs showing fluorescent intensities of FIG. 23, with the fluorescent intensity of each test group measured in the presence of 11 mM D-glucose normalized to 100 (a:Cy3-Glc-α, b:GB2-Cy3)
Figure 25:
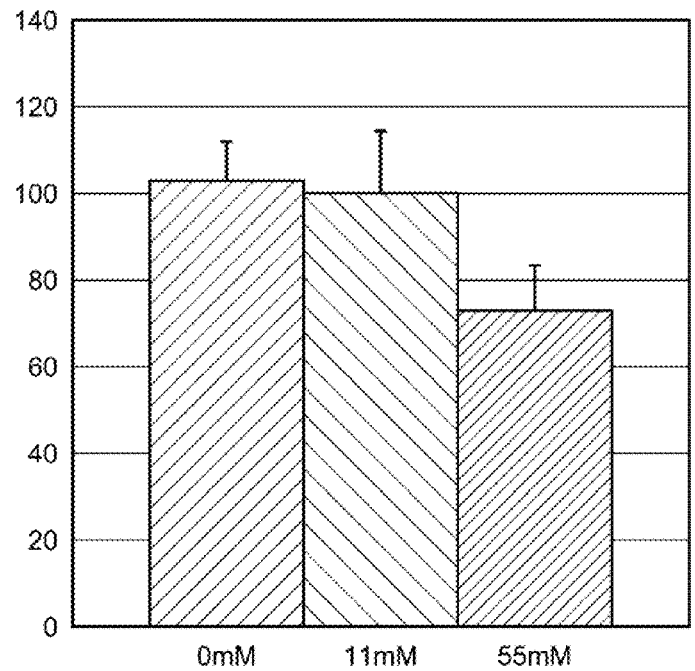

Fluorescence was observed by fluorescence imaging analysis which was performed in the same manner as in above, with the exception that A549 lung carcinoma cells were employed and 12.5 μM Cy3-Glc-α and GB2-Cy3 were used as fluorescent glucose analogues. The fluorescent images were taken and are shown in FIGS. 23 to 25.

Figure 23:
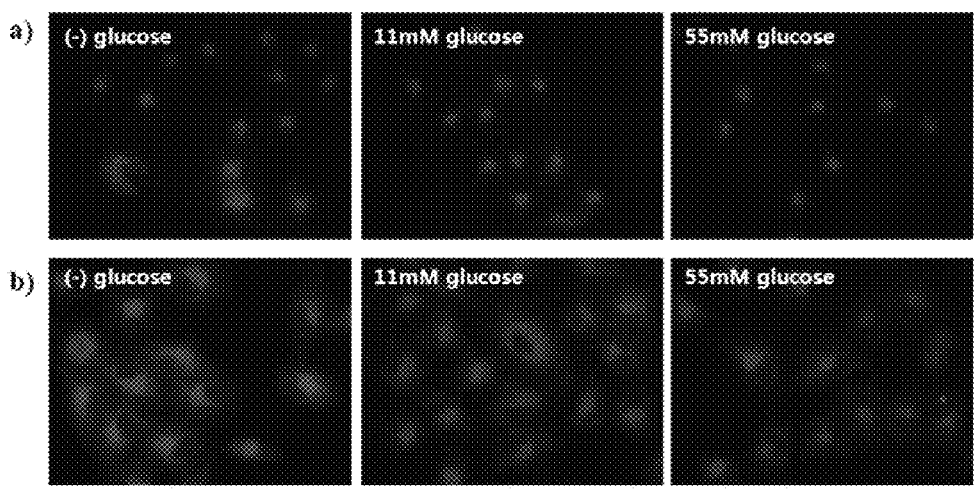
FIG. 23 is of fluorescence images showing competitive uptake of fluorescent glucose analogues (a:Cy3-Glc-α, b:GB2-Cy3, each 12.5 µM) in A549 lung carcinoma cells at various concentrations of D-glucose.
Figure 23:
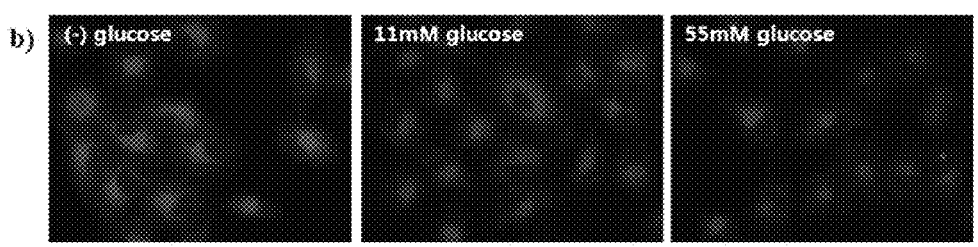

As shown in FIG. 23, both of the cell groups treated respectively with Cy3-Glc-α and GB2-Cy3 were decreased in the cellular uptake of the glucose analogues in D-glucose dose-dependent manners. The cells treated with GB2-Cy3 were visualized to have fluorescent intensity far higher than that of the other cell group. When the fluorescent intensity of the cells treated with GB2-Cy3 was normalized to 100, as seen in FIG. 24, the fluorescent intensity of the cells treated with Cy3-Glc-α was found to correspond to as low as 4. Also, when D-glucose changed in concentration from 10 mM to 55 mM, as shown in FIG. 25, Cy3-Glc-α induced only a small change in the fluorescent intensity of ROIs (approximately 5%) whereas GB2-Cy3 allowed a significant change in the fluorescent intensity of ROIs (approximately 27%). Accordingly, the inventive fluorescent glucose analogue GB2-Cy3 can be used as a more sensitive probe for monitoring glucose uptake of A549 cells.

Consequently, GB2-Cy3 is more sensitive and effective in monitoring the cellular uptake of glucose in a glucose uptake system, particularly in monitoring the introduction of glucose into cancer cells, than is Cy3-Glc-α.

Experimental Example 8

Generally, in order to completely differentiate into mature adipocytes, cells need to increase their glucose uptake. In this example, the fluorescent glucose analogue of the present invention was measured for cellular uptake in order to determine whether the fluorescent glucose analogue of the present invention acts as a bioprobe with regard to the glucose uptake of adipocytes and thus can be used for effectively monitoring the differentiation.

Figure 26:
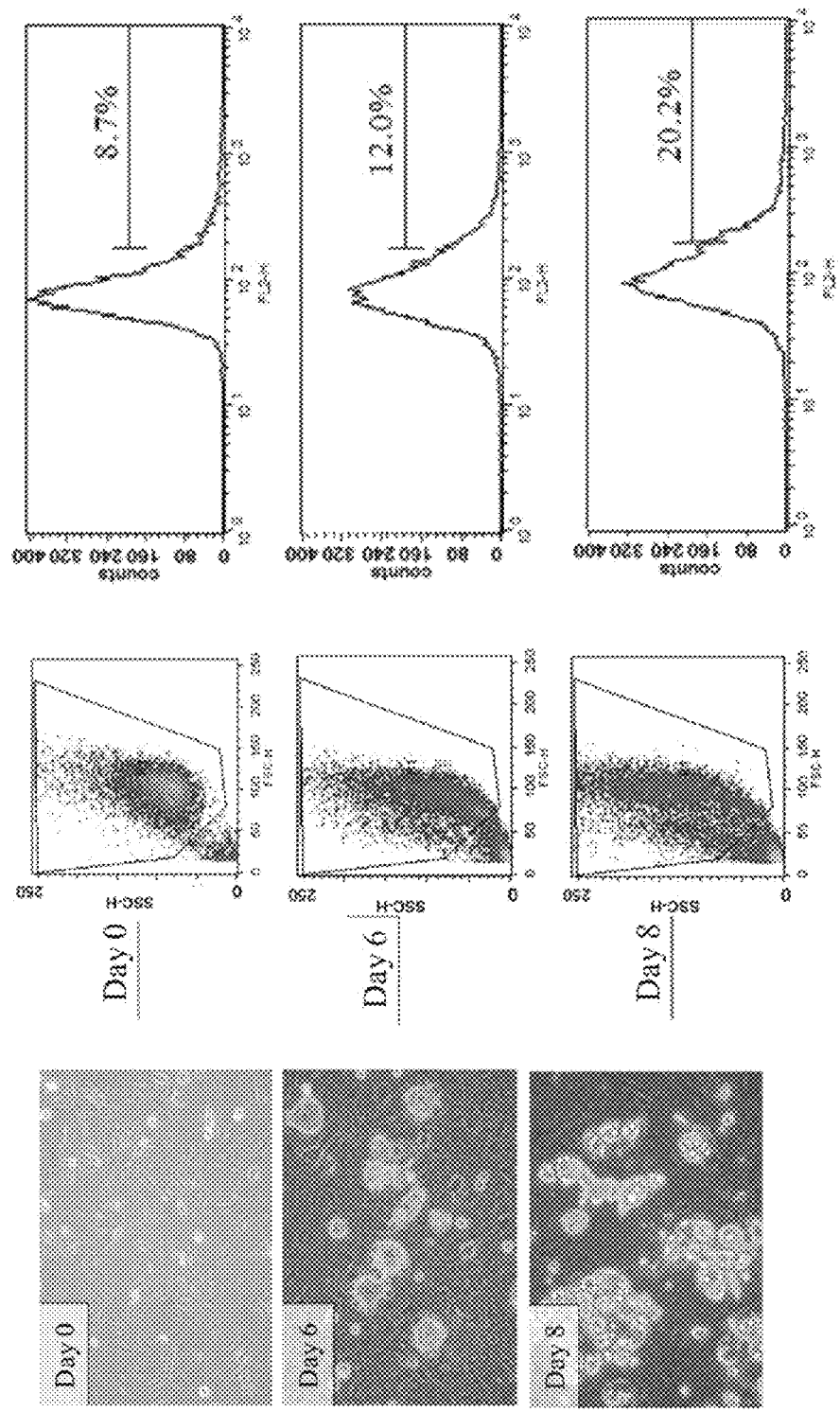
FIG. 26 is of optical microphotographs showing a change in GB2-Cy3 uptake by 3T3/L1 preadipocytes (left) and of FACS diagram plots showing the fluorescent intensity of 3T3/L1 (right) during their differentiation.

The changes in cellular glucose uptake from 3T3/L1 preadipocytes (day 0 of differentiation) toward more than 50% differentiation of mature adipocytes (day 8 of differentiation) were measured by FACS-based flow cytometric analysis using GB2-Cy3. The differentiation procedure was followed as described above. $1 \times 10^4$ cells were analyzed at FL2 channel of the flow cytometry. As the differentiation progressed, the fluorescent intensity detected by FL2 channel was increased, which indicates that the cellular uptake of glucose was effectively monitored by the fluorescent glucose analogue GB3-Cy3 (see FIG. 26). As mentioned above, the glucose analogue GB2-Cy3 of the present invention is useful for monitoring the differentiation of 3T3/L1 cells into mature adipocytes.

Experimental Example 9

In order to examine whether the fluorescent glucose analogue of the present invention effectively acts as a bioprobe for the cellular uptake of glucose, it was measured for competition with glucose for cellular uptake and uptake efficiency.

The present inventors examined the effect of competitive inhibition of D-glucose in combination with the insulin response test on C2C12 muscle cells using the reported procedures for the differentiation of C2C12 cells and the insulin stimulation (G. Portier, A. Benders, A. Oosterhof, J. Veerkamp, T. van Kuppevelt, *In Vitro Cell. Dev. Biol.-Animal* 1999, 35, 219-227; C. Wilson, Y. Mitsumoto, F. Maher, A. Klip, *FEBS Lett.* 1995, 368, 19-22].

Prior to insulin-stimulation, the cells were serum-starved with low glucose DMEM for 24 h, which was followed by 30-min incubation with insulin (170 nM). The resulting cells were incubated with 5 µM GB2-Cy3 for 15 min in the absence/presence of 11 mM D-glucose. They were washed with cold PBS, collected and analyzed using FACSCalibur™. After detection of GB2-Cy3 by FL2 channels, mean fluorescent intensity values were calculated. Fluorescence intensity was normalized with the C2C12 cells cultured in the absence of D-glucose and insulin for direct comparison, and shown in FIG. 27(b).

Figure 27:
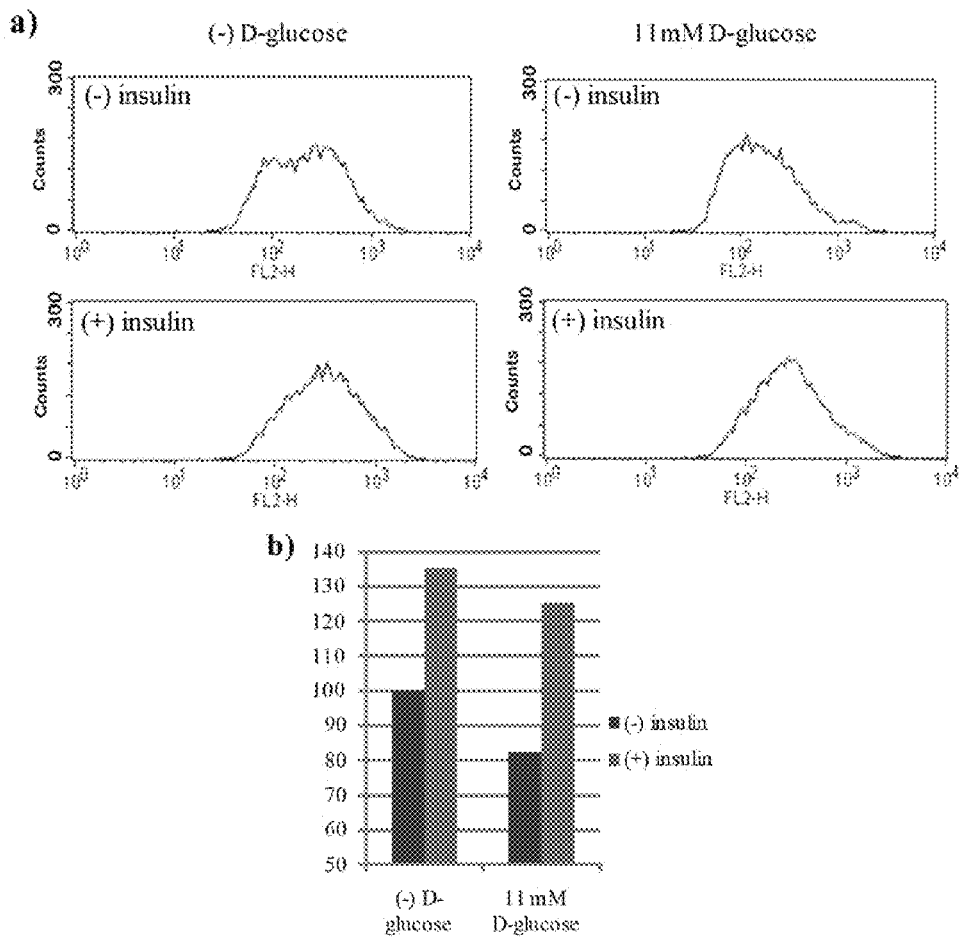
FIG. 27 is of graphs showing glucose competition and insulin response in C2C12 muscle cells treated with GB2-Cy3. a) Fluorescence intensity as analyzed by flow cytometry; b) Fluorescence intensity was normalized with the C2C12 cells cultured in the absence of D-glucose and insulin.

The increase in glucose uptake after induction by insulin treatment was observed by the changes in the competitive cellular uptake of GB2-Cy3 in C2C12 cells, as shown in FIG. 27(b). Among the several subtypes of GLUTs, GLUT4 is responsible for the insulin response in those cells, and its translocation from the intracellular compartments to the plasma membrane is predominantly controlled by insulin stimulation. In contrast, GLUT1 is constitutively expressed on the plasma membrane even in the absence of insulin stimulation, and it maintains a basal level of glucose concentration in the cytoplasm of not only in adipocytes and muscle cells but also many other cell types.

The present inventors confirmed the GLUT-specific uptake of GB2-Cy3 by increasing the concentration of D-glucose (competitive inhibition of GB2-Cy3) and observing the enhanced intracellular uptake of GB2-Cy3 by C2C12 muscle cells in response to the insulin treatment.

Experimental Example 10

Further, the present inventors investigated whether GB2-Cy3 can be used to monitor the insulin-independent enhancement of glucose uptake in cells. To this end, the present inventors selected a small-molecule activator of AMPK (AMP-activated kinase) for studying the insulin-independent mechanism. AMPK regulates ATP concentration in the cytoplasm by monitoring the ATP/AMP ratio. If the ATP/AMP-ratio is disturbed, AMPK is phosphorylated at Thr172; this phosphorylation can increase the cellular glucose uptake for ATP production via translocation of GLUT4 to plasma membrane. Therefore, AMPK serves as a potential target for diabetes treatment, and small-molecule activators of AMPK have been investigated for the development of therapeutics for diabetes. For system validation of GB2-Cy3-based flow cytometric analysis, the present inventors selected 5-aminoimidazole-4-carboxyamide (AICAR) as the small-molecule activators of AMPK that would enhance glucose uptake in an insulin-independent manner. AICAR is known as a synthetic analogue of AMP and can activate AMPK by mimicking cellular AMP without actually altering the ATP/AMP ratio. It is also known that dexamethasone inhibits the translocation of GLUT4 in adipocytes and muscle cells, and it was reported that the incubation of 3T3/L1 adipocytes with 1 µM dexamethasone for 24 h causes a 50% reduction in the cellular uptake of 2-deoxyglucose (2-DG) both at the basal level and under the insulin-stimulated condition. It was also reported that dexamethasone inhibits the cellular uptake of 2-DG under insulin-independent stimulation by 2 mM AICAR.

Therefore, the present inventors tested whether GB2-Cy3 can be used to monitor the enhanced cellular uptake of glucose in the presence of insulin (170 nM) and AICAR (1 mM) or the reduced cellular uptake of glucose in the presence of dexamethasone (1 µM). 3T3/L1 preadipocyte cells and C2C12 fibroblast cells were cultured in 24-well plates. When the cells reached 100% confluency, they started to differentiate. After the differentiation progressed sufficiently, the cells were serum-starved with low glucose DMEM (5.5 mM). They were incubated at 37° C. for 24 hrs with 1 µM dexamethasone and then for 1 hr with 170 nM insulin or 1 mM AICAR. Finally, the cells were incubated with 10 µM (3T3/L1) or 5 µM (C2C12) GB2-Cy3 for 15 min in the presence or absence of 11 mM D-glucose. The cells were washed with cold PBS and collected. $2\times10^5$ (3T3/L1) or $1\times10^5$ (C2C12) cells were analyzed using FACSCalibur™ and a confocal laser scanning microscope. After detection of GB2-Cy3 by FL2 channels, mean values of the fluorescent intensity were calculated and are given in FIG. 28. Confocal laser scanning microscope images are shown in FIG. 29.

Figure 28:
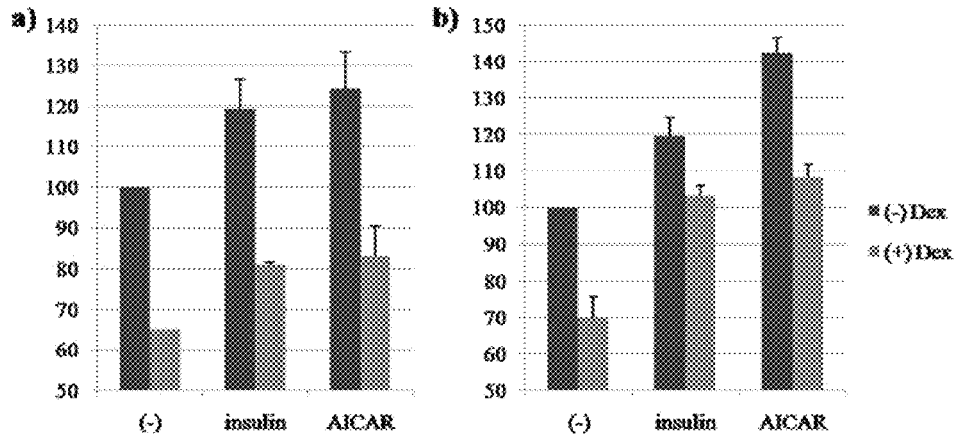
FIG. 28 is of histograms showing the cellular uptake of insulin, AICAR, and dexamethasone monitored by GB2-Cy3. Fluorescence intensity was normalized with untreated cells. a) 3T3/L1 adipocyte; b) C2C12 muscle cells
Figure 29:
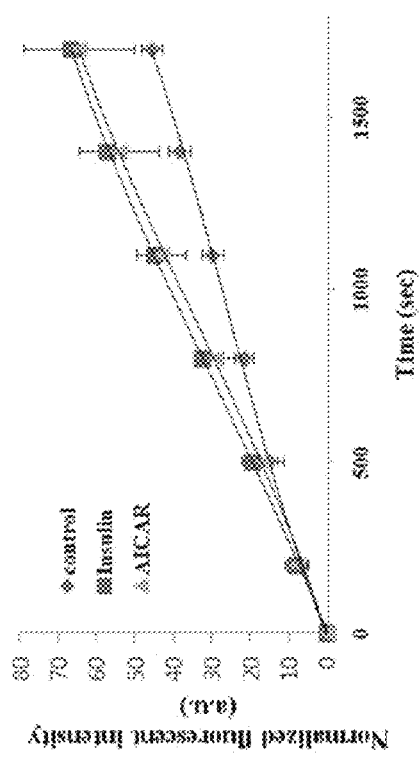
FIG. 29 is a graph and images showing the cellular uptake of insulin and AICAR monitored by GB2-Cy3 in C2C12 muscle cells by using confocal microscope. Fluorescence intensity was normalized with untreated cells. a) untreated cells; b) insulin-treated cells; c) AICAR-treated cells.
Figure 29:
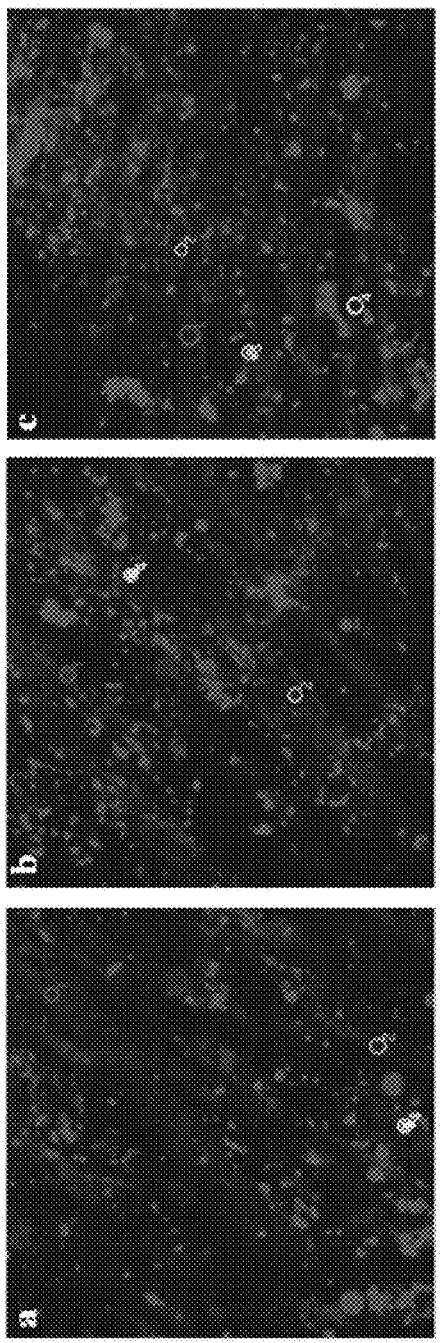

As seen in FIGS. 28 and 29, the use of GB2-Cy3 as a fluorescent bioprobe clearly demonstrated the enhanced cellular uptake under insulin- and AICAR-stimulated conditions in both 3T3/L1 adipocytes and C2C12 muscle cells. The treatment with dexamethasone effectively reduced the cellular uptake of glucose as demonstrated by GB2-Cy3 in all the cases, i.e., at the basal level, and under insulin- and AICAR-stimulated conditions.

As described hitherto, the fluorescent glucose analogue according to the present invention is a novel material that has excellent performance as a glucose uptake probe as compared to known 2-NBDG and that can monitor glucose uptake in a normal medium environment, unlike the 2-NBDG or N-2-glycosylated analogue. Serving as a bioprobe that competes with glucose for intracellular uptake, the fluorescent glucose analogue of the present invention can be applied to the monitoring of the intracellular uptake of glucose and screening of curative or preventive drugs for glucose metabolism-related diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A fluorescent glucose analogue, represented by Formula 1 or Formula 2:

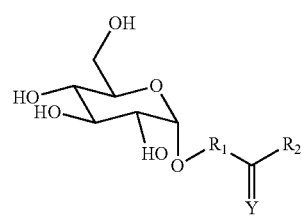

[Formula 1]

[Formula 2]
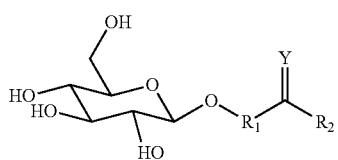
wherein
$R_1$ is —$(CH_2)_n$-A-, wherein n is an integer of from 1 to 10, and A is piperazine;
$R_2$ is —$(CH_2)_4$-Cy3; and
Y is O.
2. The fluorescent glucose analogue according to claim 1, being represented by the following Chemical Formula 5
[Chemical Formula 5]
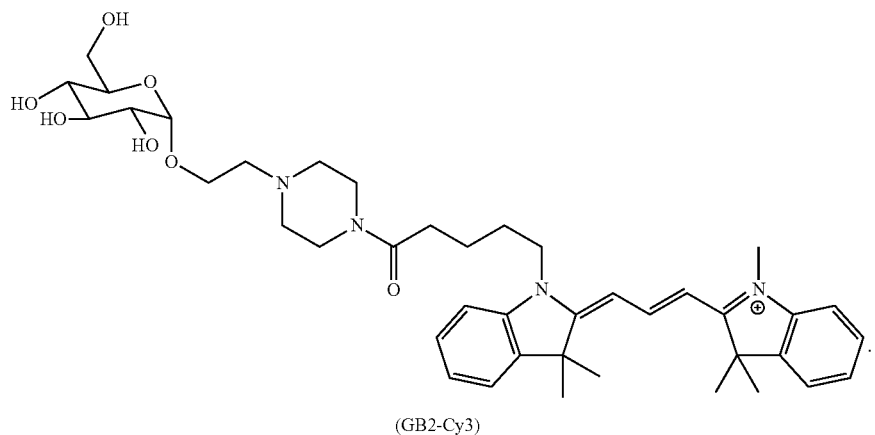
(GB2-Cy3)
3. A bioprobe, comprising the fluorescent glucose analogue of claim 1.
* * * * *